US011771398B1

(12) United States Patent
Patil et al.

(10) Patent No.: US 11,771,398 B1
(45) Date of Patent: Oct. 3, 2023

(54) FETAL HEART RATE TRANSDUCER

(71) Applicant: Aronix LLC, Peachtree Corners, GA (US)

(72) Inventors: Arun Narayan Patil, Winder, GA (US); Anand Raghunath Bhave, Pune (IN); Sunanda Narayan Patil, Pune (IN); Pratibha Narayan Patil, Pune (IN)

(73) Assignee: Aronix LLC, Peachtree Corners, GA (US)

( * ) Notice: Subject to any disclaimer, the term of this patent is extended or adjusted under 35 U.S.C. 154(b) by 0 days.

(21) Appl. No.: 18/074,222

(22) Filed: Dec. 2, 2022

(51) Int. Cl.
*A61B 8/08* (2006.01)
*A61B 8/00* (2006.01)
*B06B 1/02* (2006.01)
*B06B 1/06* (2006.01)

(52) U.S. Cl.
CPC .......... *A61B 8/0866* (2013.01); *A61B 8/0883* (2013.01); *A61B 8/54* (2013.01); *A61B 8/587* (2013.01); *B06B 1/0215* (2013.01); *B06B 1/0633* (2013.01); *B06B 2201/76* (2013.01)

(58) Field of Classification Search
CPC combination set(s) only.
See application file for complete search history.

(56) References Cited

U.S. PATENT DOCUMENTS

| | | | |
|---|---|---|---|
| 8,696,578 B2 * | 4/2014 | Kabakov | A61B 8/40 600/453 |
| 2010/0168596 A1 * | 7/2010 | Jaeschke | A61B 8/5276 600/511 |
| 2010/0274145 A1 * | 10/2010 | Tupin, Jr. | A61B 5/0022 600/511 |
| 2013/0123637 A1 * | 5/2013 | Wohlschlager | A61B 8/02 600/453 |
| 2013/0158407 A1 * | 6/2013 | Kabakov | A61B 8/0866 600/453 |
| 2013/0245436 A1 * | 9/2013 | Tupin, Jr. | A61B 5/6833 600/430 |
| 2014/0276070 A1 * | 9/2014 | Kabakov | A61B 5/02411 600/453 |
| 2016/0213349 A1 * | 7/2016 | Groberman | A61B 8/02 |
| 2022/0142476 A1 * | 5/2022 | Nair | A61B 5/344 |

* cited by examiner

*Primary Examiner* — Sanjay Cattungal
(74) *Attorney, Agent, or Firm* — H. Brock Kolls

(57) ABSTRACT

The present invention relates to an improved fetal heart rate transducer that overcomes shortcomings of prior transducers in several ways including utilizing an ultra slow-cure epoxy in combination with a piezo-electric disc bonding method to improve ultrasound transmission and reception characteristics, utilizing a slow-cure epoxy in combination with a frontend PCB bonding method to improve transducer reliability, utilizing a metal insert design in combination with molding-in techniques versus press fitting to improve the mechanical stability of the transducer, and utilizing a failsafe LVDS circuit to improve cable error detection and thus improve fetal monitor system reliability. In addition, a method of use of the present invention includes quantitively determining the integrity of each of the piezo-electric disc bonds with the plastic substrate as well as the integrity of the ultrasound field using various height water phantoms that simulate the human body.

21 Claims, 29 Drawing Sheets

Fig. 1
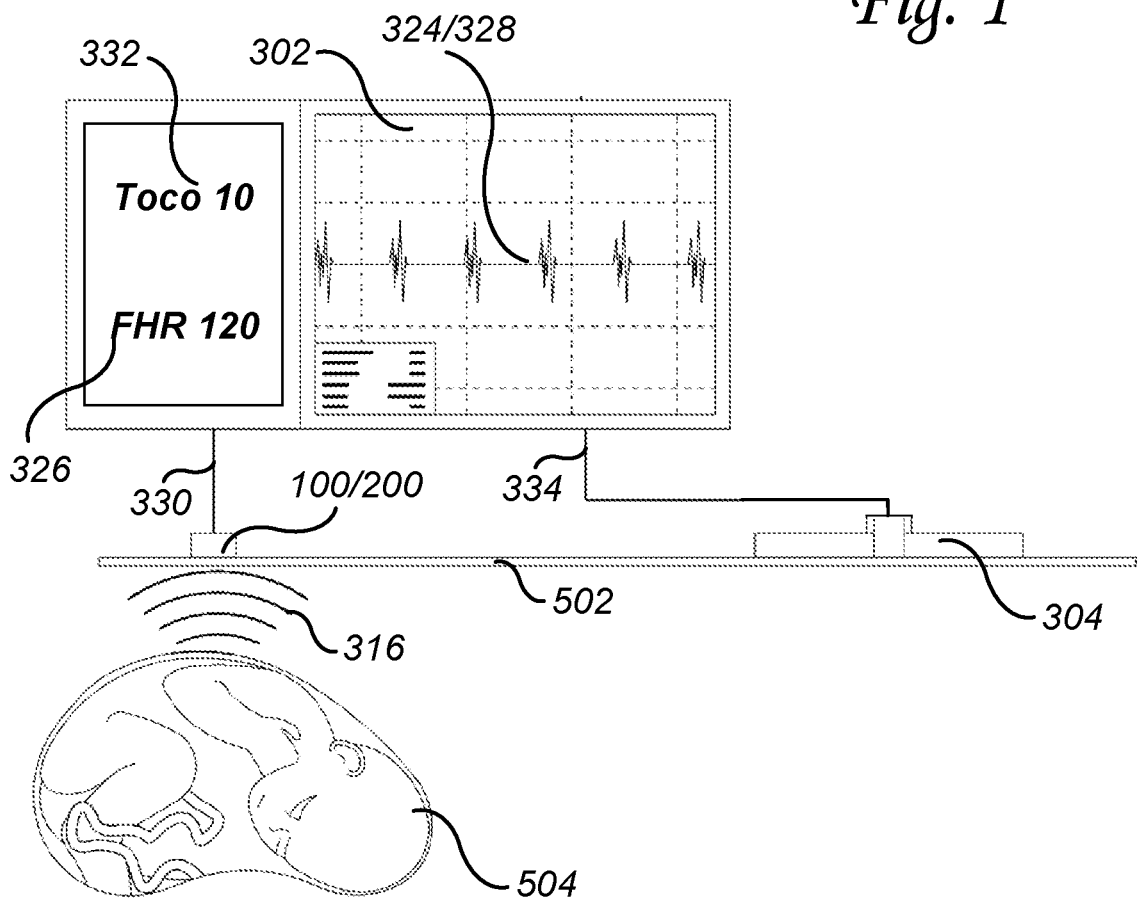
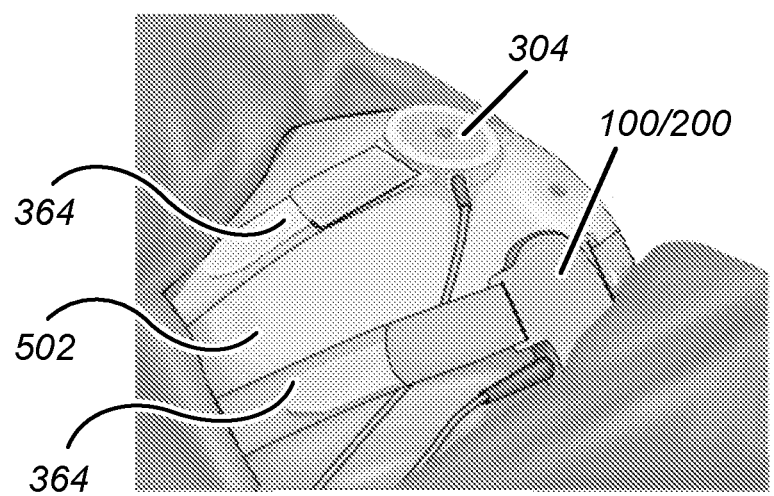

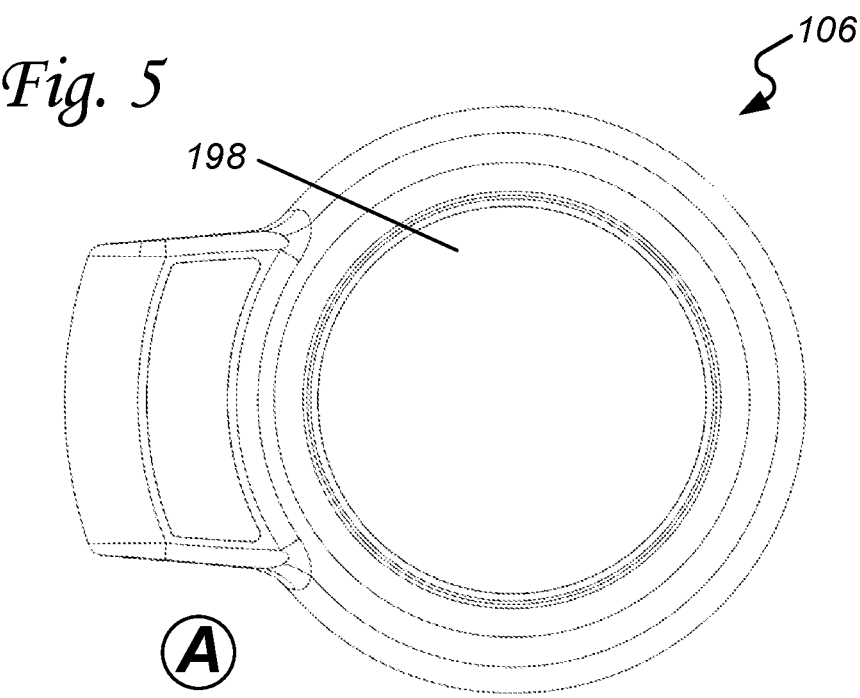
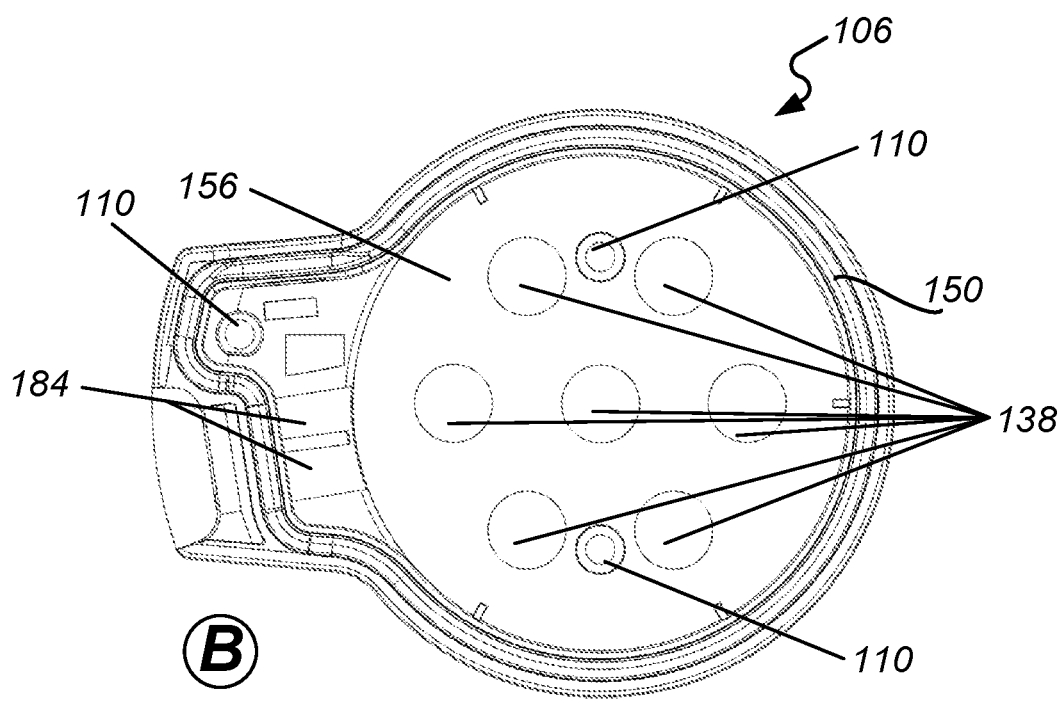
Fig. 5

*Fig. 6*
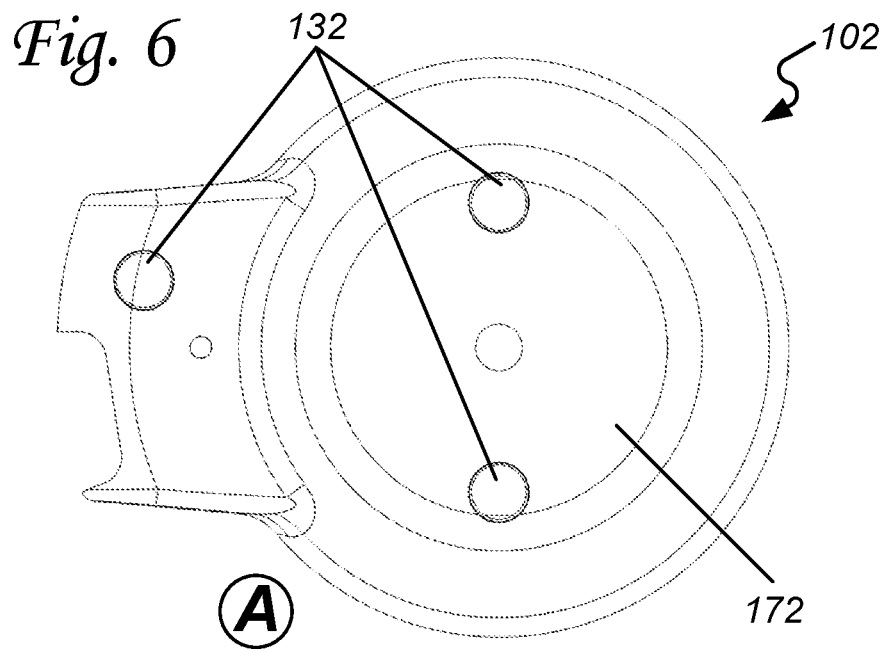
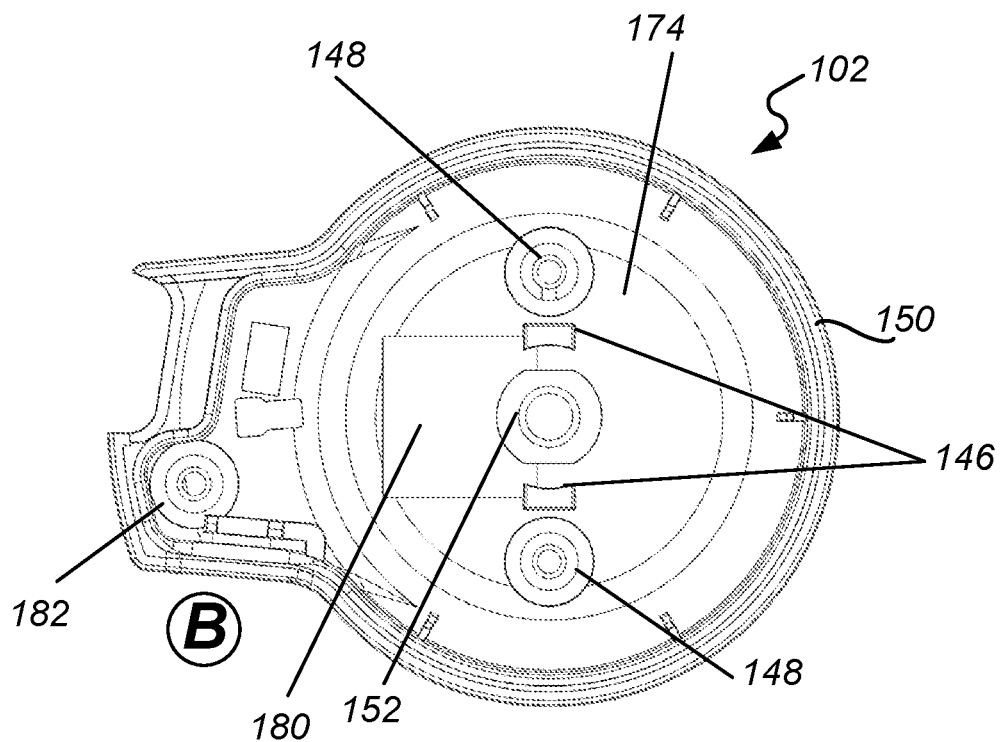

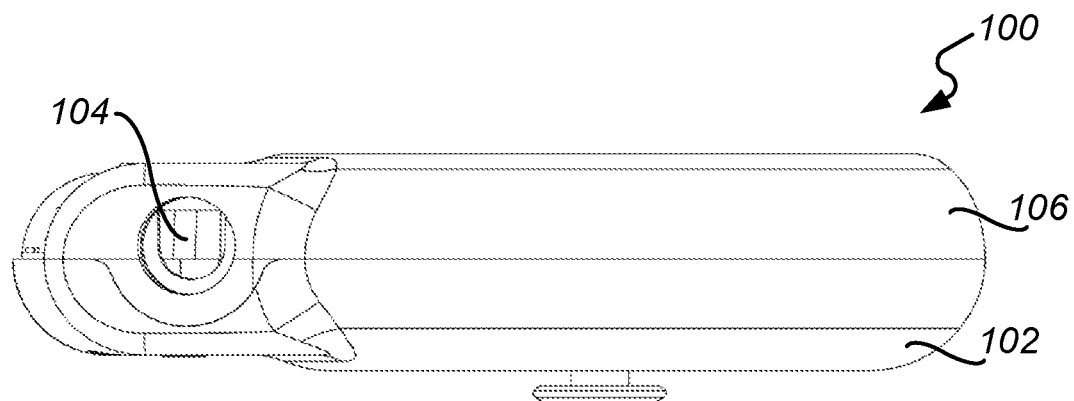
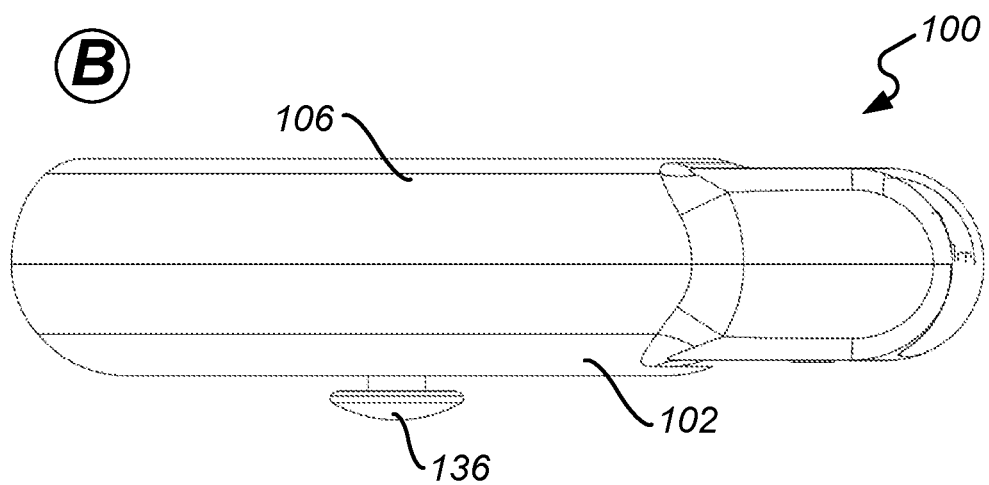
Fig. 7

*Fig. 8*
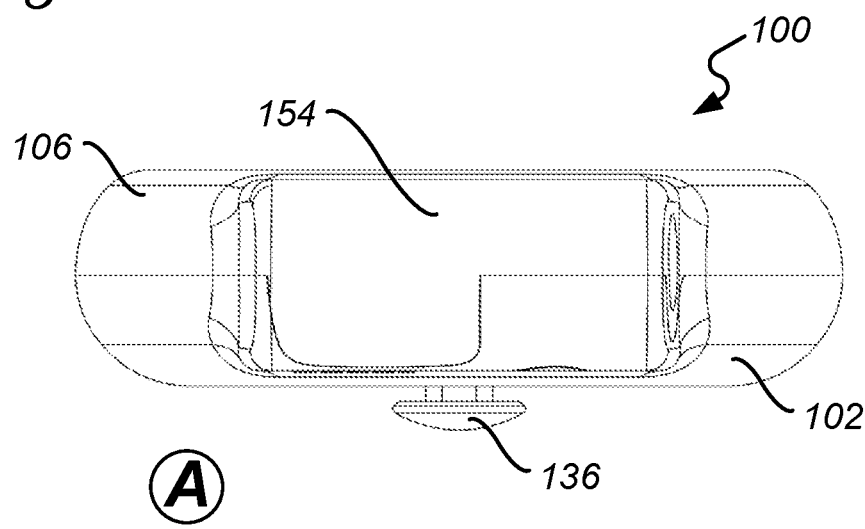
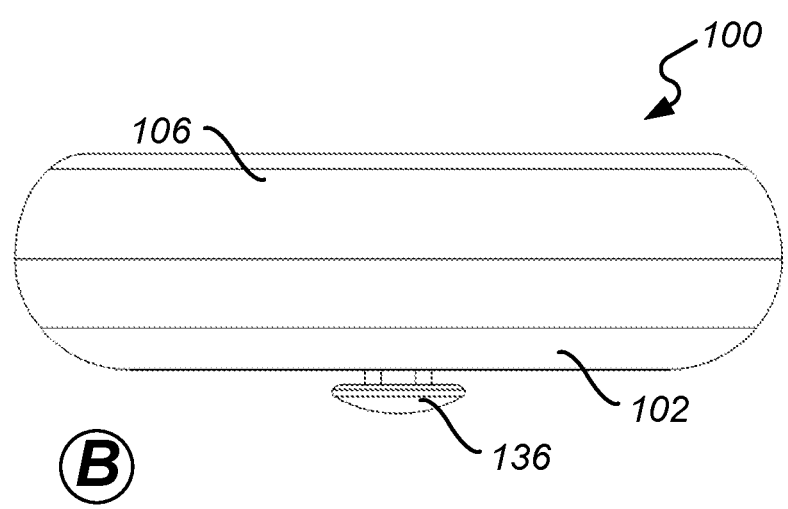

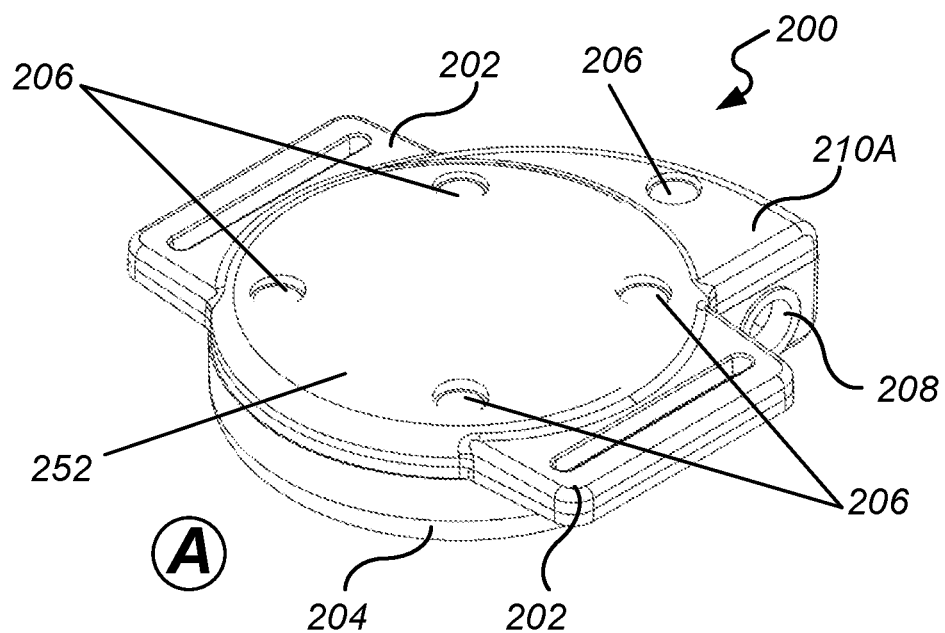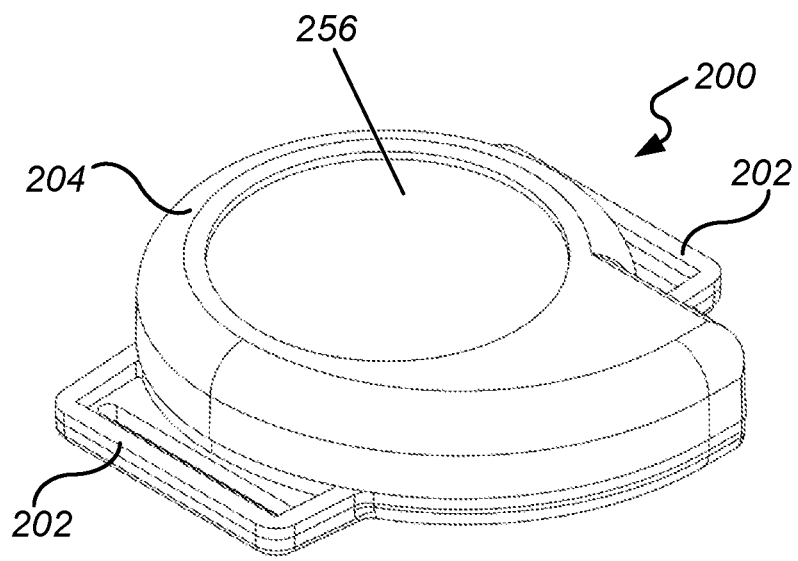
Fig. 10

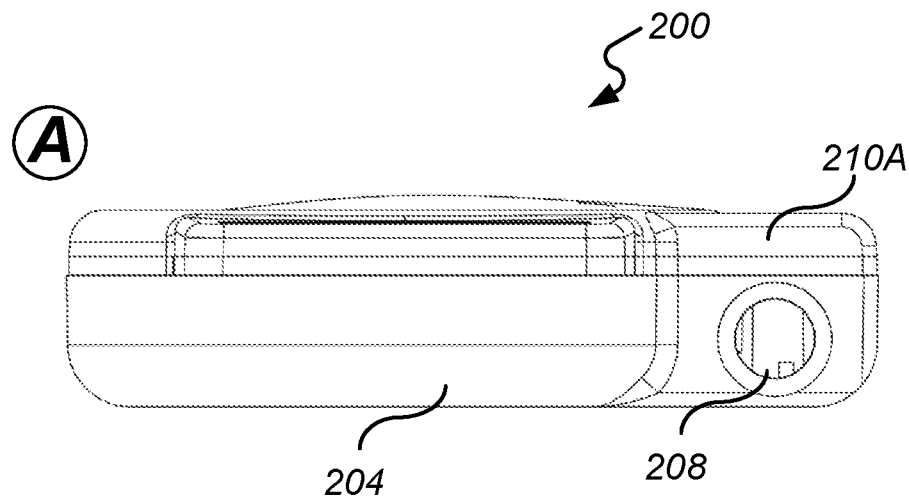
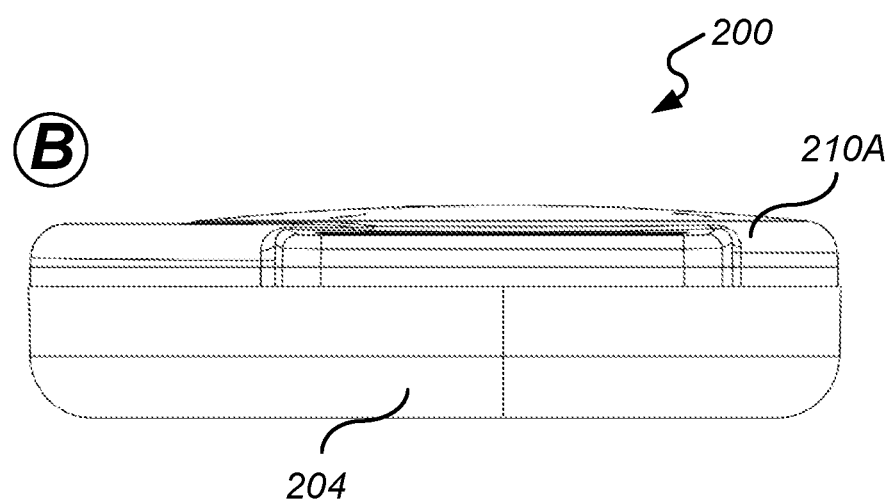
Fig. 14

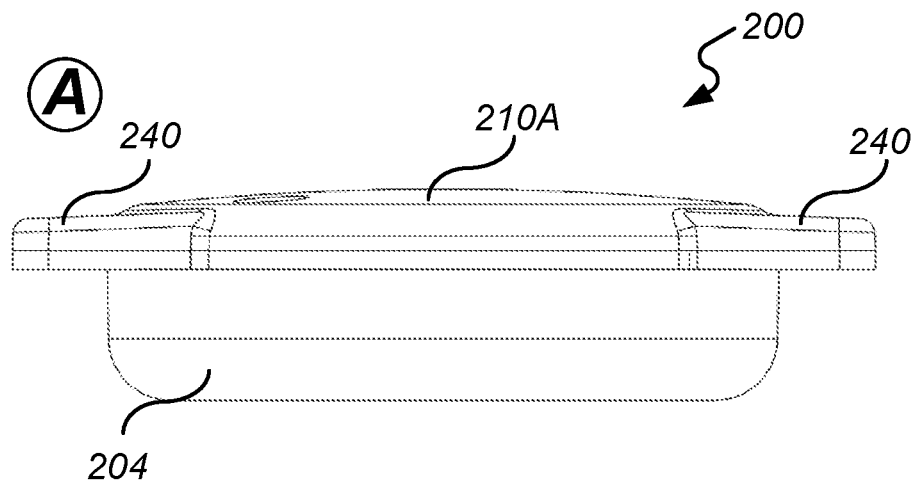
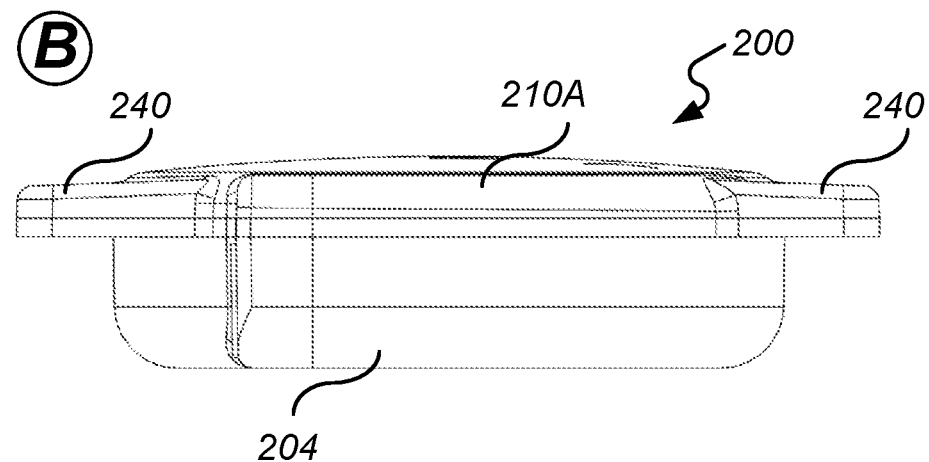
Fig. 15

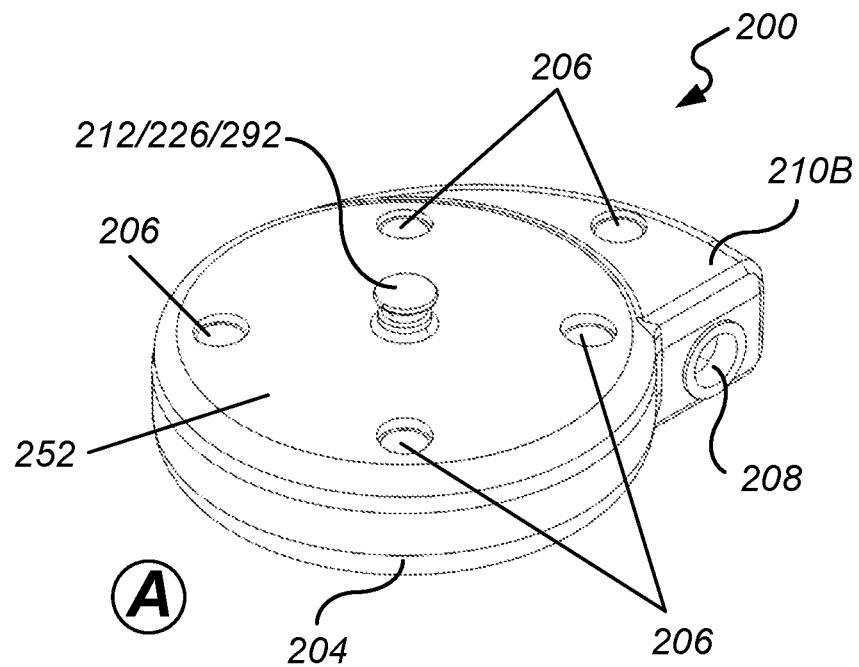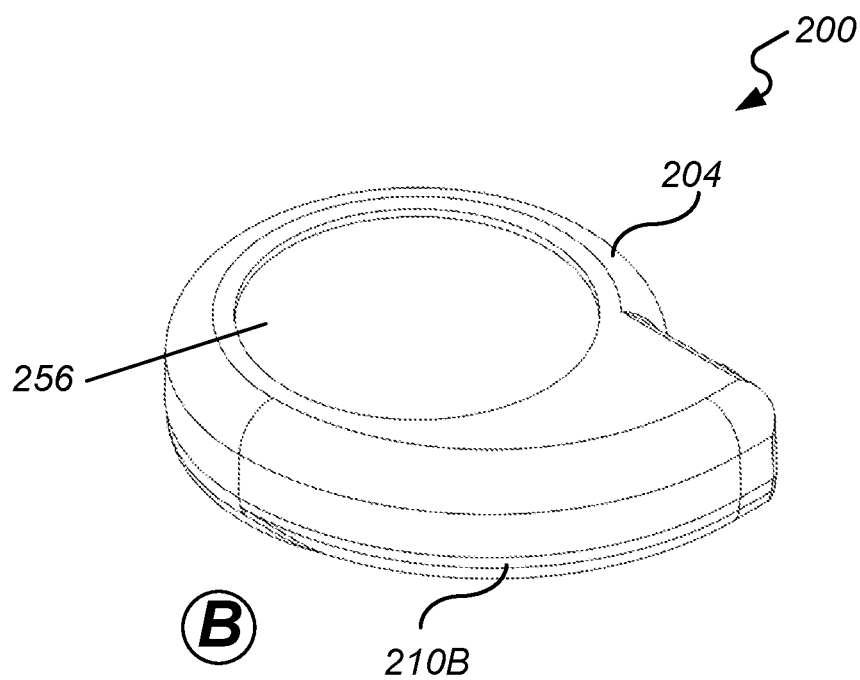
Fig. 17

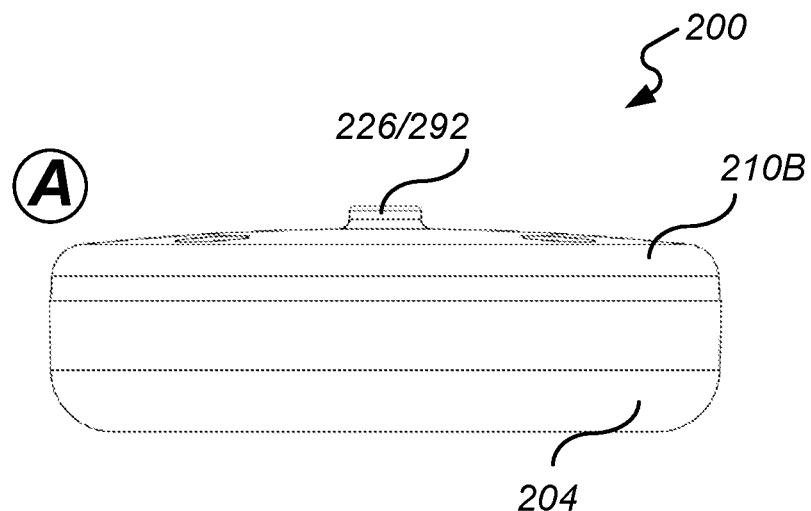
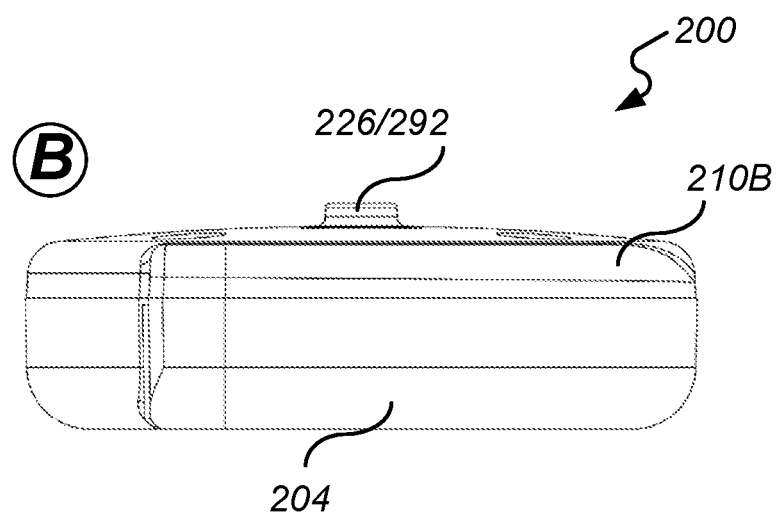
Fig. 20

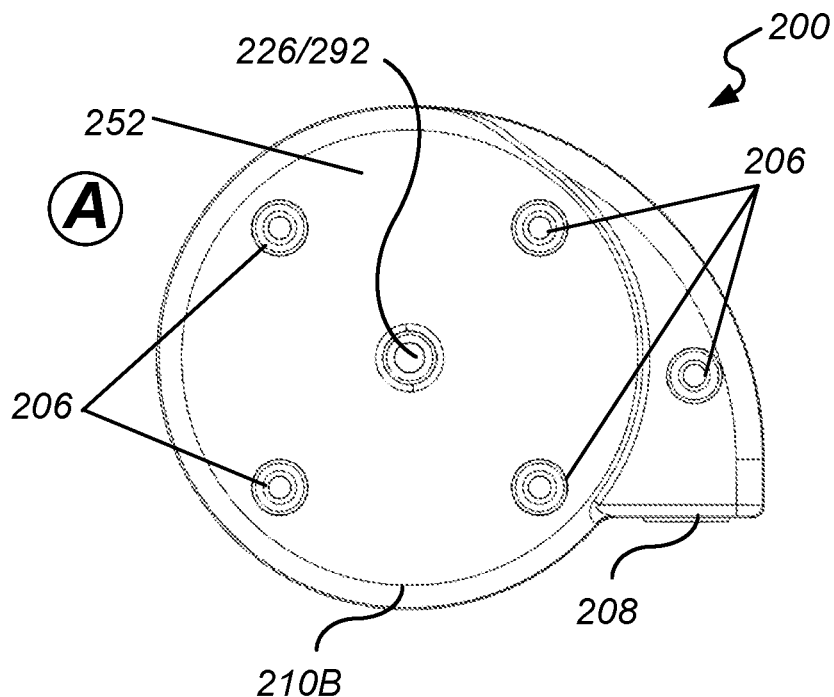
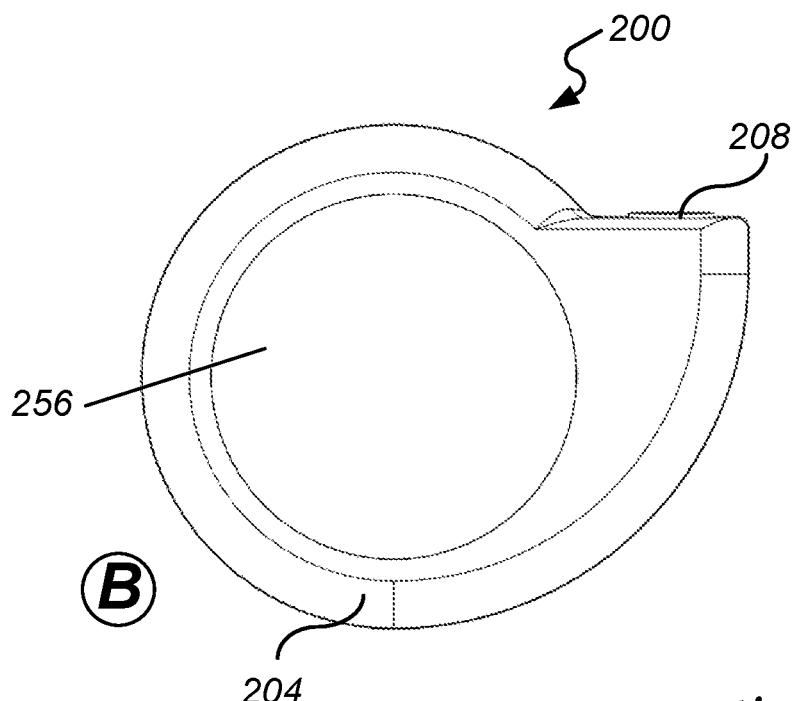
Fig. 21

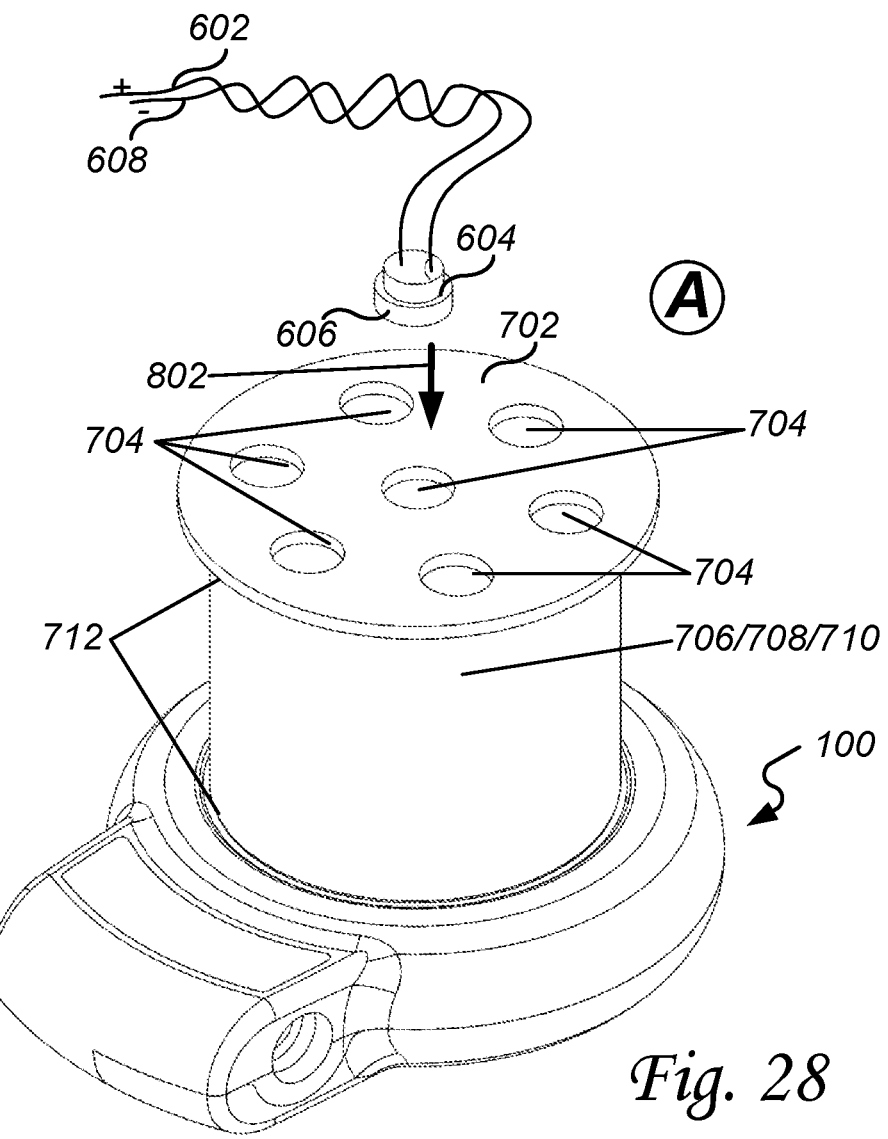
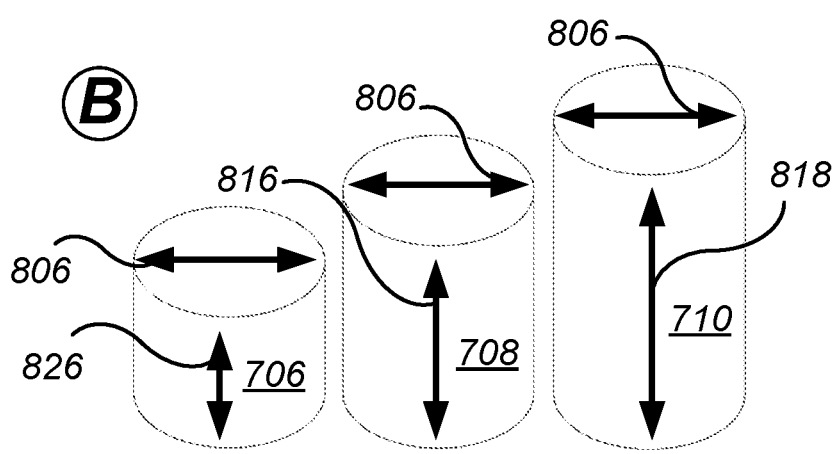
Fig. 28

| | | Emitted | | Propagating | | Observed | |
|---|---|---|---|---|---|---|---|
| Source | Observer | freq. | wave length | freq. | wave length | freq. | wave length |
| • | • | $n$ | $\lambda$ | $n$ | $\lambda$ | $n$ | $\lambda$ |
| $V_s \rightarrow$ | • | $n$ | $\lambda$ | $\dfrac{nv}{v-v_s}$ | $\left(\dfrac{v-v_s}{v}\right)\lambda$ | $\dfrac{nv}{v-v_s}$ | $\left(\dfrac{v-v_s}{v}\right)\lambda$ |
| $\leftarrow V_s$ | • | $n$ | $\lambda$ | $\dfrac{nv}{v+v_s}$ | $\left(\dfrac{v+v_s}{v}\right)\lambda$ | $\dfrac{nv}{v+v_s}$ | $\left(\dfrac{v+v_s}{v}\right)\lambda$ |
| • | $\leftarrow V_o$ | $n$ | $\lambda$ | $n$ | $\lambda$ | $\left(\dfrac{v+v_o}{v}\right)n$ | $\left(\dfrac{v}{v+v_o}\right)\lambda$ |
| • | $V_o \rightarrow$ | $n$ | $\lambda$ | $n$ | $\lambda$ | $\left(\dfrac{v-v_o}{v}\right)n$ | $\left(\dfrac{v}{v-v_o}\right)\lambda$ |
| $V_s \rightarrow$ | $\leftarrow V_o$ | $n$ | $\lambda$ | $\dfrac{nv}{v-v_s}$ | $\dfrac{v-v_s}{v}\lambda$ | $\left(\dfrac{v+v_o}{v-v_s}\right)n$ | $\left(\dfrac{v-v_s}{v+v_o}\right)\lambda$ |
| $V_s \rightarrow$ | $V_o \rightarrow$ | $n$ | $\lambda$ | $\dfrac{nv}{v-v_s}$ | $\dfrac{v-v_s}{v}\lambda$ | $\left(\dfrac{v-v_o}{v-v_s}\right)n$ | $\left(\dfrac{v-v_s}{v-v_o}\right)\lambda$ |
| $\leftarrow V_s$ | $\leftarrow V_o$ | $n$ | $\lambda$ | $\dfrac{nv}{v+v_s}$ | $\left(\dfrac{v+v_s}{v}\right)\lambda$ | $\left(\dfrac{v+v_o}{v+v_s}\right)n$ | $\left(\dfrac{v+v_s}{v+v_o}\right)\lambda$ |
| $\leftarrow V_s$ | $V_o \rightarrow$ | $n$ | $\lambda$ | $\dfrac{v}{v+v_s}n$ | $\dfrac{v+v_s}{v}\lambda$ | $\left(\dfrac{v-v_o}{v+v_s}\right)n$ | $\left(\dfrac{v+v_s}{v-v_o}\right)\lambda$ |

*Fig. 30*

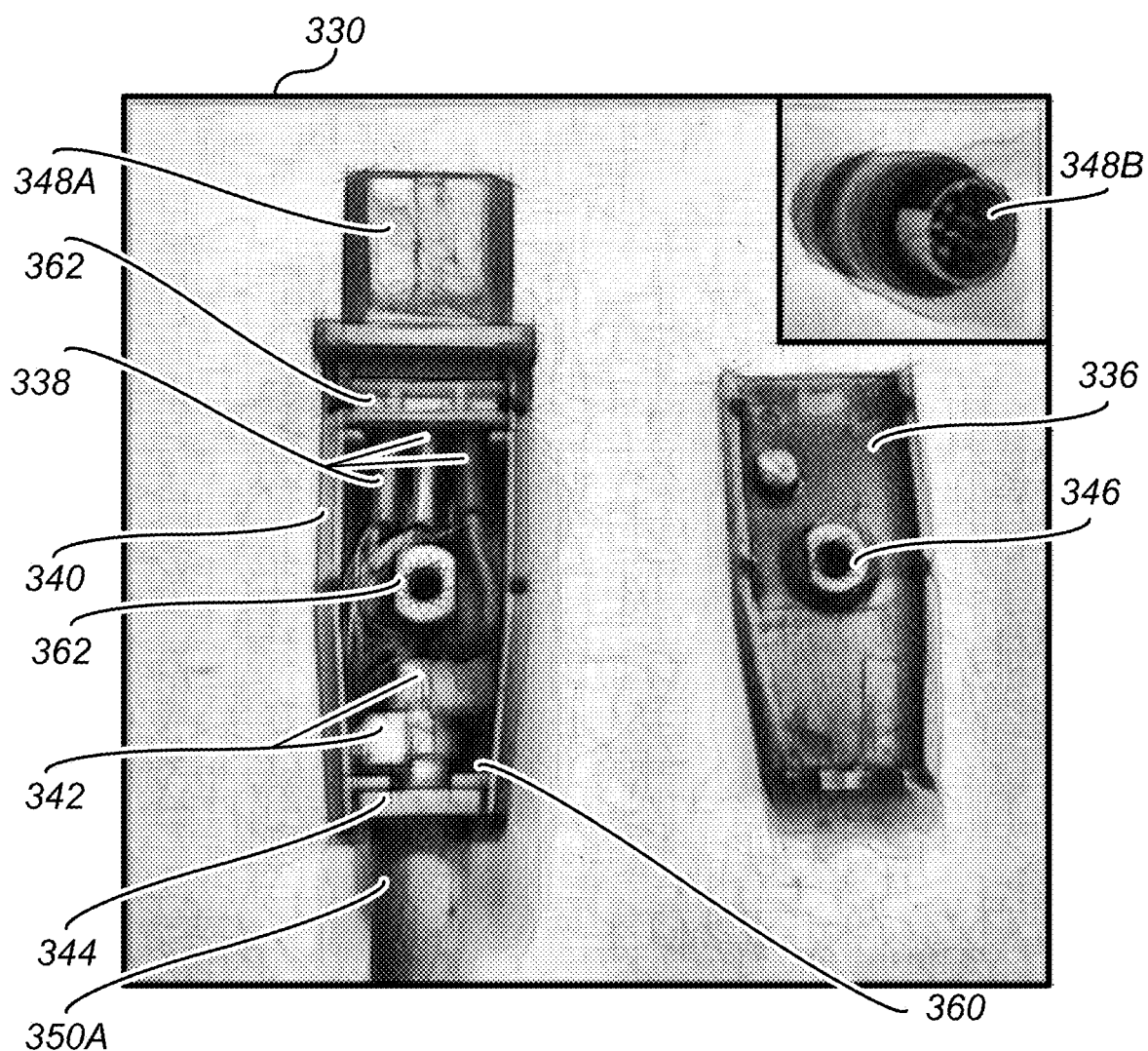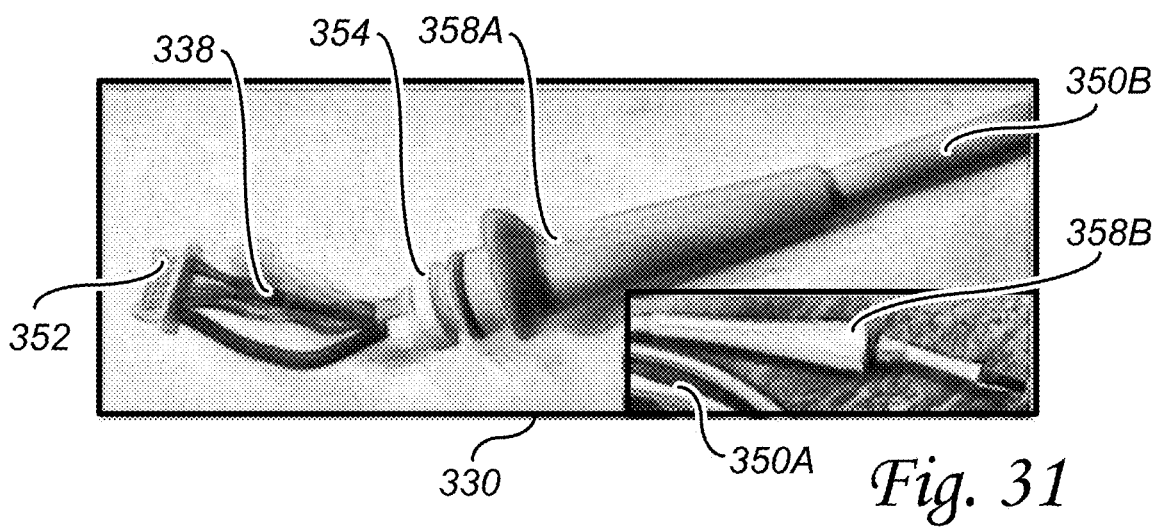
Fig. 31

US 11,771,398 B1

FETAL HEART RATE TRANSDUCER

TECHNICAL FIELD OF THE INVENTION

This invention relates to an improved fetal heart rate transducer, and particularly to an improved fetal heart rate transducer that overcomes shortcomings of prior transducers through component bonding techniques, mechanical reliability improvements, cable fault failsafe error detection, and methods of use that enable quantitative integrity assessment of each piezo-electric disc bond, and ultrasound field integrity assessment using water phantoms that simulate the human body.

BACKGROUND OF THE INVENTION

Before our invention in gynecology and obstetrics, one of the medical parameters important in assessing the condition of a fetus is the fetal heart rate measured by way of an ultrasound Doppler signal. Such fetal heart rate systems typically comprise a fetal heart rate transducer that is operationally coupled to a fetal heart rate monitor (fetal monitor/Cardiotocograph or CTG Machine). The fetal heart rate transducer is placed on the patient's stomach proximate to the fetus.

A shortcoming of prior fetal heart rate transducers is the bonding characteristics of the piezo-electric crystals (PZT) discs with the plastic resin used in creating the external transducer housing. In this regard, the PZT discs have a high acoustic impedance and hence their bonding to the plastic resin enclosure requires a very thin homogeneous layer of conformal adhesive that remains intact without change in acoustic properties over variation of temperatures (room temp, body temp, after contact to abdomen skin, etc.) and application of hygroscopic gel for coupling the ultrasonic wavefront (beam) to human tissue. Such characteristics are not present in current PZT crystal bonding techniques and as a result, a common failure of the fetal heart rate transducer is PZT discs separating from the plastic resin surface partially or entirely which creates signal degradation and spurious FHR readings rendering the transducer inoperable.

Another shortcoming of prior fetal heart rate transducers is the cracking and degradation of the standoffs that are molded into the plastic resin case. In this regard, either self-tapping screws are threaded into plastic standoffs or metal inserts are pressed into the standoffs. In both cases, the stress introduced in the plastic standoffs over time leads to the cracking of the plastic standoffs and the loosening of the self-tapping screws, the printed circuit board (PCB) secured by the screws, and other components. Such loosening of the PCB and other components allows motion of these items as the patient breathes or moves, which is detected by the PZT discs causing inaccurate fetal heart rate readings.

Another shortcoming is that prior to our invention there wasn't a way to quantitatively test the integrity of the adhesive bond between the PZT discs and the plastic resin enclosure. Additionally, there wasn't a way to quantitively measure the ultrasound field strength and operational characteristics of PZT discs individually and/or in operational combination with the plurality of PZT discs within a fetal heart rate transducer.

Another shortcoming of prior fetal heart rate transducers is in the signal processing capabilities. In this regard, loose, broken, open, or shorted wire connections between the fetal heart rate transducer and the fetal monitor can be misreported and therefore cause inaccurate or intermittent fetal heart rate readings.

The present invention addresses these and other shortcomings by providing an improved fetal heart rate transducer. For these reasons and shortcomings as well as other reasons and shortcomings there is a long-felt need that gives rise to the present invention

SUMMARY OF THE INVENTION

The shortcomings of the prior art are overcome and additional advantages are provided through the provision of an improved fetal heart rate transducer comprising a top case, an ultra slow-cure epoxy, and a bottom case that fastens to the top case. The bottom case comprises an interior surface. The interior surface comprises more than one standoff, and de-embossed or raised more than one piezo-electric crystal (PZT) pad.

The improved fetal heart rate transducer further comprises more than one metal insert that is molded into place within the standoff as the bottom case is fabricated, and more than one PZT disc having a top side and an epoxy side. Each of the PZT discs adheres to the PZT pads as follows: cleaning the interior surface and the PZT discs with mild soap solution, rinsing with deionized/distilled water, and air drying. The ultra slow-cure epoxy is mixed and degassed in a vacuum for a first degas time period. Depositing a drop of the ultra slow-cure epoxy in the center of the epoxy side of each of the PZT discs while the PZT discs are resting on a horizontal surface with the epoxy side up, or the PZT pad while the bottom case is resting on a horizontal surface. Allowing the drop to self-level for the first self-leveling time period. The epoxy side of each of the PZT discs is placed on each of the PZT pads while the bottom case is resting on a horizontal surface. And, allowing the PZT disc and the bottom case assembly to cure for a first cure time period.

Additional shortcomings of the prior art are overcome and additional advantages are provided through the provision of an improved fetal heart rate transducer comprising a top case, and a bottom case that fastens to the top case. The bottom case comprises an interior surface. The interior surface comprises more than one standoff, and de-embossed or raised more than one piezo-electric crystal (PZT) pad.

The improved fetal heart rate transducer further comprises more than one metal insert that is molded into place within the standoff as the bottom case is fabricated, and more than one PZT disc having a top side and an epoxy side. Each of the PZT discs are adhered to the PZT pads.

The improved fetal heart rate transducer further comprises an electronic control and signal processing system. The electronic control system, the electronic control system comprises a low voltage differential signal (LVDS) receiver having an IN+ input, an IN− input, and an output, the LVDS receiver monitors the operational status of the improved fetal heart rate transducer by generating at the output a first logic state or a second logic state as follows: when the difference between the IN+ and the IN− is greater than or equal to 100 mv the output is the first logic state; when the difference between the IN+ and the IN− is less than or equal to 100 mv the output is the second logic state; when the IN+ is open (not connected) the output is the first logic state; when the IN− is open (not connected) the output is the first logic state; when the IN+ and IN− are connected by a first resistance, that is configured as an undriven parallel termination, the output is the first logic state; when IN+ is shorted to Vcc or ground the output is the first logic state; when IN− is shorted to Vcc or ground the output is the first logic state; and when IN+ and IN− are shorted together the output is the first logic state. Wherein the first logic state is either high or low and the second logic state is the opposite of the first logic state. Wherein the first logic state is latched on the output, requiring corrective action and power reset to clear latching of the output when the first logic state persists on the output for more than a predetermined error condition time period.

Additional shortcomings of the prior art are overcome and additional advantages are provided through the provision of a method of using an improved fetal heart rate transducer comprising the steps of coupling an index plate with an ultrasound coupling jelly to an improved fetal heart rate transducer. The index plate has more than one piezo-electric crystal (PZT) disc position hole corresponding to and correlated with the locations of each of more than one PZT disc within the improved fetal heart rate transducer. The improved fetal heart rate transducer comprises a top case and a bottom case that fastens to the top case. The bottom case comprises an interior surface. The interior surface comprises more than one standoff, and de-embossed or raised more than one piezo-electric crystal (PZT) pad. More than one metal insert is molded into place within the standoff as the bottom case is fabricated.

More than one PZT disc has a top side and an epoxy side. Each of the PZT discs adheres to the PZT pad as follows: cleaning the interior surface and the PZT disc with mild soap solution, rinsing with deionized/distilled water, and air drying. Mixing and degassing in a vacuum, for a first degas time period, an ultra slow-cure epoxy. Depositing a drop of the ultra slow-cure epoxy in the center of the epoxy side of each of the PZT discs while the PZT discs are resting on a horizontal surface with the epoxy side up, or the PZT pad while the bottom case is resting on a horizontal surface. Allowing the drop to self-level for the first self-leveling time period. Placing the epoxy side of each of the PZT discs on each of the PZT pads while the bottom case is resting on a horizontal surface. And, allowing the PZT disc and the bottom case assembly to cure for a first cure time period.

The method continues by recording a transducer PZT disc transmit waveform for each of the PZT discs, by way of an oscilloscope that is operationally connected to a hydrophone that is in a receive mode, by placing a hydrophone PZT disc that is operationally related to the hydrophone into one of the PZT disc position holes and recording one of the transducer PZT disc transmit waveform corresponding to one of the PZT discs, and repeating by moving the hydrophone PZT disc to a different one of the PZT disc position holes until at least one of the transducer PZT disc transmit waveform has been recorded at each of the PZT disc position holes. And, determining if each of the transducer PZT disc transmit waveform is similar in amplitude, frequency, and repetition rate indicating that the improved fetal heart rate transducer is transmitting properly, and indicating that each of the PZT discs is uniformly bonded to the interior surface of the bottom case of the improved fetal heart rate transducer.

Additional shortcomings of the prior art are overcome and additional advantages are provided through the provision of an improved fetal heart rate transducer comprising a top case, and a bottom case that fastens to the top case, the bottom case comprises an interior surface, the interior surface comprises de-embossed or raised more than one piezo-electric crystal (PZT) pad.

The improved fetal heart rate transducer comprises more than one PZT disc, each PZT disc adheres to the PZT pad, and a frontend printed circuit board (PCB) is secured to the bottom case and is operationally related to the PZT disc. A cable has a first cable end and a second cable end. A fetal monitor end/side connector comprises a hollow rigid body having a wire connection end and an integrally formed grooved. A strain relief is placed over the first cable end and secured within the integrally formed grooved end holding the first cable end from slipping out of the hollow rigid body. And, a secondary strain relief is fastened around the first cable end within the hollow rigid body proximate to the strain relief. Wherein the tie wraps further prevent the first cable end from being pulled out of the hollow rigid body, more than one conductor from the first cable end terminates with electrical connections at the wire connection end. Wherein the fetal monitor connector plugs into a fetal monitor, and the second cable end terminates with a transducer connector, the transducer connector connects to the frontend PCB.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 illustrates one example of a fetal monitor and placement of an improved fetal heart rate transducer and a tocodynamometer transducer on a patient;

FIGS. 5-9 illustrate examples of an improved fetal heart rate transducer;

FIG. 10 illustrates one example of a perspective view of an improved fetal heart rate transducer that comprises more than one belt slot;

FIGS. 12-16 illustrate examples of an improved fetal heart rate transducer belt loop style;

FIGS. 17-21 illustrate examples of an improved fetal heart rate transducer belt button style;

FIG. 28 illustrates one example of a hydrophone used in combination with a plurality of water phantoms;

FIG. 30 illustrates one example of Doppler equations for frequency shift calculations; and FIG. 31 illustrates one example of a cable assembly.

DETAILED DESCRIPTION OF THE INVENTION

Figure 2:
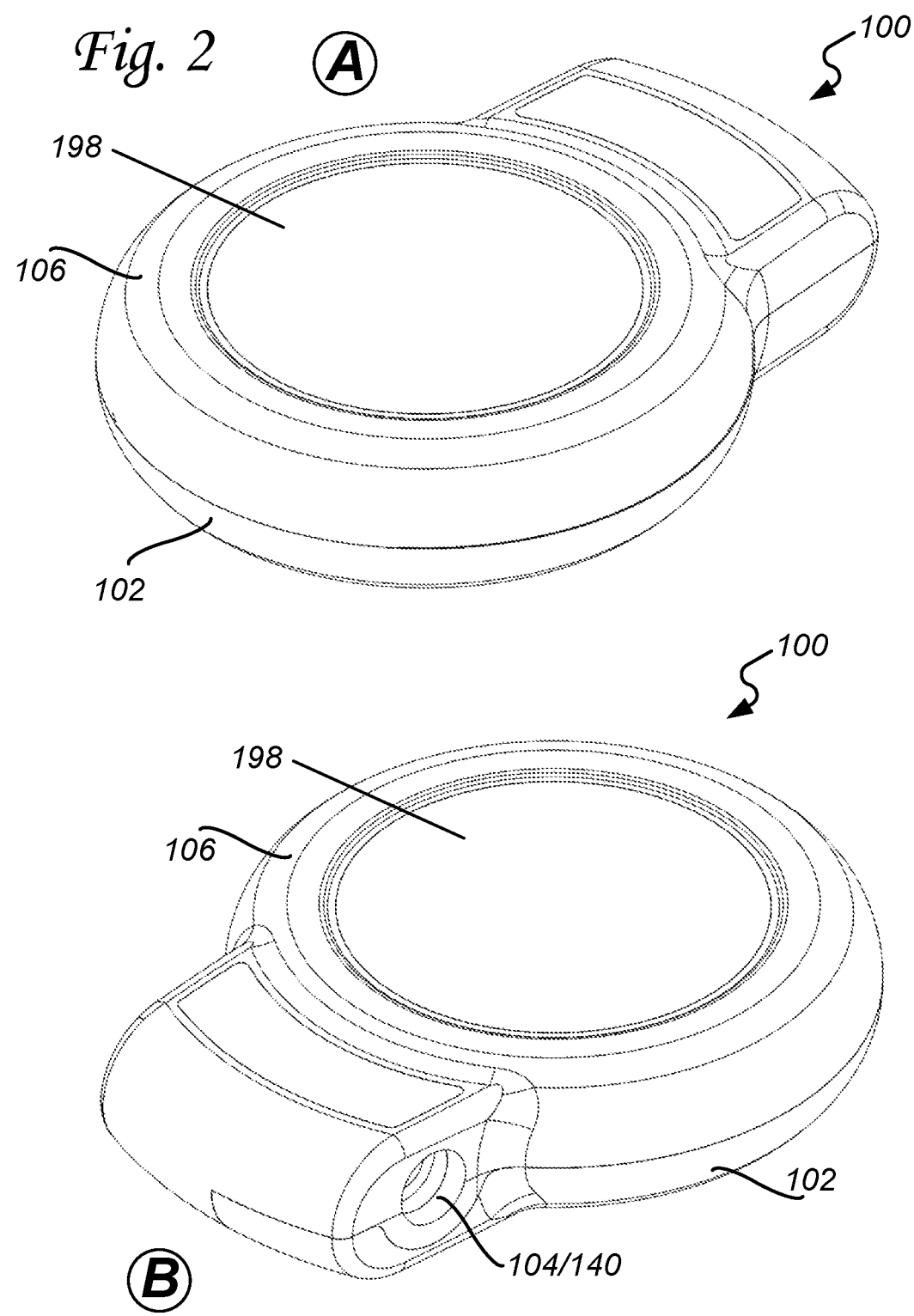
FIG. 2 illustrates one example of a bottom perspective view of an improved fetal heart rate transducer.

The detailed description explains the preferred embodiments of the invention, together with advantages and features, by way of example with reference to the drawings.

For pre-birth applications, the most common method to obtain fetal heart rate is by using an ultrasound (US) transducer which is to be placed externally on the pregnant woman's abdomen. The ultrasound signal is received by piezo-electric crystals Lead Zirconate Titanate/PZT Discs and appropriately filtered. As the heart rate signal is contained in the very noisy received ultrasound Doppler signal, the ultrasound transducer must be placed directly over the fetal heart of the fetus which is approximately located on the lower left part of the abdomen.

Industry ultrasound transducers include Philips Avalon models M2736A, M2736AA, M2726A, Ref #867246, Avalon CL Ref #866076, and preceding HP medical model M1356A, 15245A. These models of transducers use 7 PZT (Lead Zirconate Titanate) discs in each transducer that are 10 millimeters (mm) in diameter with a center resonant frequency of 1 MHz (+/−100 Hz).

Other industry ultrasound transducers include the GE Corometrics model 5700AAX (Belt Loop Style), 5700BAX (Belt Button Style), NAUTILUS 5700LAX (Belt Loop Style), NAUTILUS 5700HAX (Belt Button Style) and Ref #2108346-001 (Combo/Belt Button and Loop Style). These models of transducers use 9 PZT (Lead Zirconate Titanate) discs that are 11.9 mm in diameter with a center resonant frequency of 1.151 MHz.

In operation, PZT discs vibrate in thickness mode (transverse/along the axis) when excited with respective frequency signals and produce an ultrasonic beam in two directions along the perpendicular axis of the PZT discs, one in the front surface that is coupled to the abdomen of the patient and a second in the opposite direction inside the transducer head cavity towards the top plastic case. The excitation pulse of 1 MHz with a repetition rate of 3 kHz is applied in Philips ultrasound transducers and 1.15 MHz with a repetition rate of 2 kHz or 4 kHz (depending on single or dual Channel use and the fetal monitor model) is applied in GE Corometrics Nautilus transducers. The same PZT discs act as transmitters as well as receivers of the reflected ultrasonic pulse waveform (echo signal).

Philips transducers have 7 PZT discs glued to the plastic surface. The frontend printed circuit board (PCB) is glued to the plastic surface and the backend PCB is mounted on top of the frontend PCB (models M2736A, M2736AA, M2726A, Ref #867246, and Avalon CL Ref #866076) by way of two dual header connectors that are in the direct pathway of the ultrasound beam emitted from the PZT discs. In these models, the PZT discs and frontend PCB are adhered to the plastic surface using a one-part silicone adhesive.

The frontend PCB has a pulse transmit-receiver, decoupling circuit, amplifier, and filter circuit to process ultrasound echo signals received from the beating fetal heart. The output analog signal (Doppler shift signal) is proportional to the rate of movement of the fetal heart. The backend PCB comprises the central processing unit (CPU) which converts analog Doppler signal to a digital signal that represents the fetal heart rate (FHR). The digital signal is communicated to a Philips Avalon fetal monitor (model FM 20, 30, 40, or 50) by way of a cable using a CAN (controlled area network) protocol or wirelessly for Philips model M2726A and Ref #866076.

Corometrics transducer models 5700AAX, 5700BAX, NAUTILUS 5700LAX, NAUTILUS 5700HAX, and Ref #2108346-001 have 9 PZT discs glued to the plastic surface and a frontend PCB mounted with self-tapping aluminum screws on stand-offs (without threaded metal inserts) above the 9 PZT discs. For these models of transducers, the frontend PCB doesn't have any active circuit component but rather only a single in-line nine-segment 47 ohm resistor network. A coaxial cable connects the transducer to the GE Corometrics fetal monitor through a 12-pin circular connector where 3 connections are for actual signal transmission and one short link across 2 pins of the connectors which is used for transducer recognition. For these models of transducers, the bottom side of the frontend PCB is a shield plane (connected to earth ground on the fetal monitor) to minimize stray electric field coupling to the PZT discs. The center core of the coaxial cable has two conductors, a positive signal conductor is connected to all 9 PZT discs' positive electrodes through the 47 ohm resistor network, and a negative signal conductor is connected to the negative electrode of the PZT disc. In these models, the PZT discs are adhered to the plastic surface using a one-part silicone adhesive.

The prior industry transducer models mentioned above have a number of shortcomings that are overcome in the present invention. Such shortcomings include intermittent signals or spurious noise that can be characterized by bonding that fails and standoffs that crack due to press-fitted metal inserts or self-tapping screws that allow the PZT discs and frontend PCB to become loose or vibrate, and an inability to detect cable wire shorts, breaks, and intermittent disconnects. Such intermittent signal misbehavior due to these and other shortcomings can cause the transducer not to work at all, or perhaps worse display the wrong fetal heart rate such as excessively high or low heart rates when connected to the patient as well as when not connected to the patient at all.

In general, the ultrasound Doppler signal requires complex electrical signal processing and filtering due to the very noisy (EMI) environment in hospitals as various electronic and RF communication equipment are used in the vicinity.

The present invention overcomes prior transducer shortcomings of ultrasound Doppler signal inaccuracy and transducer reliability through a number of improvements. These improvements include transducer mechanical stability, ultrasound accuracy by way of improved PZT disc bonding with the transducer enclosure, cable fault/failsafe detection electrical circuit improvements, and methods of use. In this regard, the present invention, overcomes the fundamental shortcomings of prior industry transducer models 15245A, M1356A, Avalon M2736A, M2736AA, Ref #867246, Avalon CTS M2726A, Avalon CL Ref #866076, and GE Corometrics models 5700AAX, 5700BAX, NAUTILUS 5700LAX, NAUTILUS 5700HAX, NAUTILUS Ref #2108346-001. The improved fetal heart rate transducer 100/200 operates and functions in strict adherence to basic pulse Doppler principles to provide consistent and accurate fetal heart rate (FHR) detection by eliminating all the root causes/sources of the intermittent/spurious behavior of prior industry transducers. The advantages, in the present invention, improves fetal heart transducer FHR detection reliability, and transducer durability reducing costs and equipment downtime making it easier to use for both the patient as well as the clinical end user.

For disclosure purposes, the improved fetal heart rate transducer 100/200 can be referred to as improved fetal heart rate transducer 100, improved fetal heart rate transducer 200, the fetal heart rate transducer 100/200, the fetal heart rate transducer 100, the fetal heart rate transducer 200, transducers 100/200, transducer 100, or transducer 200.

Another advantage, in the present invention, is to rectify the fundamental design shortcomings in Philips fetal ultrasound transducer models 15245A, M1356A, Avalon M2736A, M2736AA, Ref #867246, Avalon CTS M2726A, Avalon CL Ref #866076, GE Corometrics ultrasound model 5700AAX, 5700BAX, NAUTILUS 5700LAX, NAUTILUS 5700HAX and NAUTILUS Ref #2108346-001 to provide a continuous measurement of FHR without spurious readings to provide reliable data for patient management.

Another advantage, in the present invention, is to provide a plurality of methods of use, one of which includes a quantitative ultrasound integrity assessment procedure to assess the performance of PZT discs after bonding to the plastic surface and the accuracy of each of the PZT disc output as a basic sensor (transmitter and receiver of ultrasound wave/beam) element.

Another advantage, in the present invention, is to provide a comprehensive design shortcoming correction process for physically intact OEM transducers (with 100% OEM parts from Philips/GE-Corometrics) that is less expensive and more reliable than the new replacement from the respective manufacturers that have fundamental design shortcomings that result in performance issues, especially spurious FHR readings.

Turning now to the drawings in greater detail, it will be seen that in FIG. 1 there is illustrated one example of a fetal monitor 302 and placement of an improved fetal heart rate transducer and a tocodynamometer transducer on a patient 502. In an exemplary embodiment, a fetal monitor 302 can be interconnected with an improved fetal heart rate transducer 100/200 by way of a cable 330 or wirelessly. The transducer 100/200 can be secured to the abdomen of patient 502 by a belt 364 proximate to fetus 504. The belt can secure a transducer by way of a button 136/212 style attachment or as shown in FIG. 1 with a belt loop 202 style attachment.

A tocodynamometer (Toco) transducer 304 can also be interconnected by a cable 334 or wireless connection with a fetal monitor. In this regard, the fetal monitor can display both the Toco 332 readings as well as the fetal heart rate (FHR) 326 and associated Toco waveforms 324 as well as the FHR waveform 328.

In an exemplary embodiment, the ultrasound transducer 100/200 construction comprises either 7 or 9 PZT discs 112/218. It is connected to the fetal monitor 302 through a shielded cable 330. A signal of 1 or 1.15 MHz from a stable frequency generator is applied to PZT discs 112/218 for about 100 microseconds and then the timing control circuit switches the PZT discs 112/218 to a receiving mode for about 200 microseconds. The received signal is operationally coupled to a preamplifier. The pulsed transmission and reception continue with a fixed repetition rate. The preamp output represents the received ultrasound echo signal with Doppler shift frequencies proportional to the fetal heart beating of fetus 504. The preamp output signal is conditioned through a phase discriminator/detector to extract the Doppler shift frequency envelope, digitized through an A/D converter, filtered, and finally processed either directly by microcontroller 408 or through one more preceding stage of digital signal processor (DSP) or field programmable gate array (FPGA) or a complex programmable logic device (CPLD), or other suitable circuit block implementation to strike the balance between the cost and performance for digital signal processing. The microcontroller (MCU) then outputs the results to peripheral units such as a display, strip chart recorder, speaker, or other peripheral units as may be required and/or desired in a particular embodiment.

Referring to FIG. 2, there is illustrated one example of a bottom perspective view of an improved fetal heart rate transducer 100. Reference 'A' is a front view and reference 'B' is a back view. The improved fetal heart rate transducer 100 comprises a top case 102, a bottom case 106, and a cable connector 104 hole/cavity for cable 330 strain relief 354 and PCB connector 352. The cable connector 104/140 secures one end of cable 330 to the improved fetal heart rate transducer 100. The other end of cable 330 plugs into the fetal monitor 302.

In an exemplary embodiment, the top case 102 and the bottom case 106 can be manufactured from plastic or other suitable materials. Additionally, the top case 102 and the bottom case 106 can be over-molded with polyurethane rubber.

Figure 3:
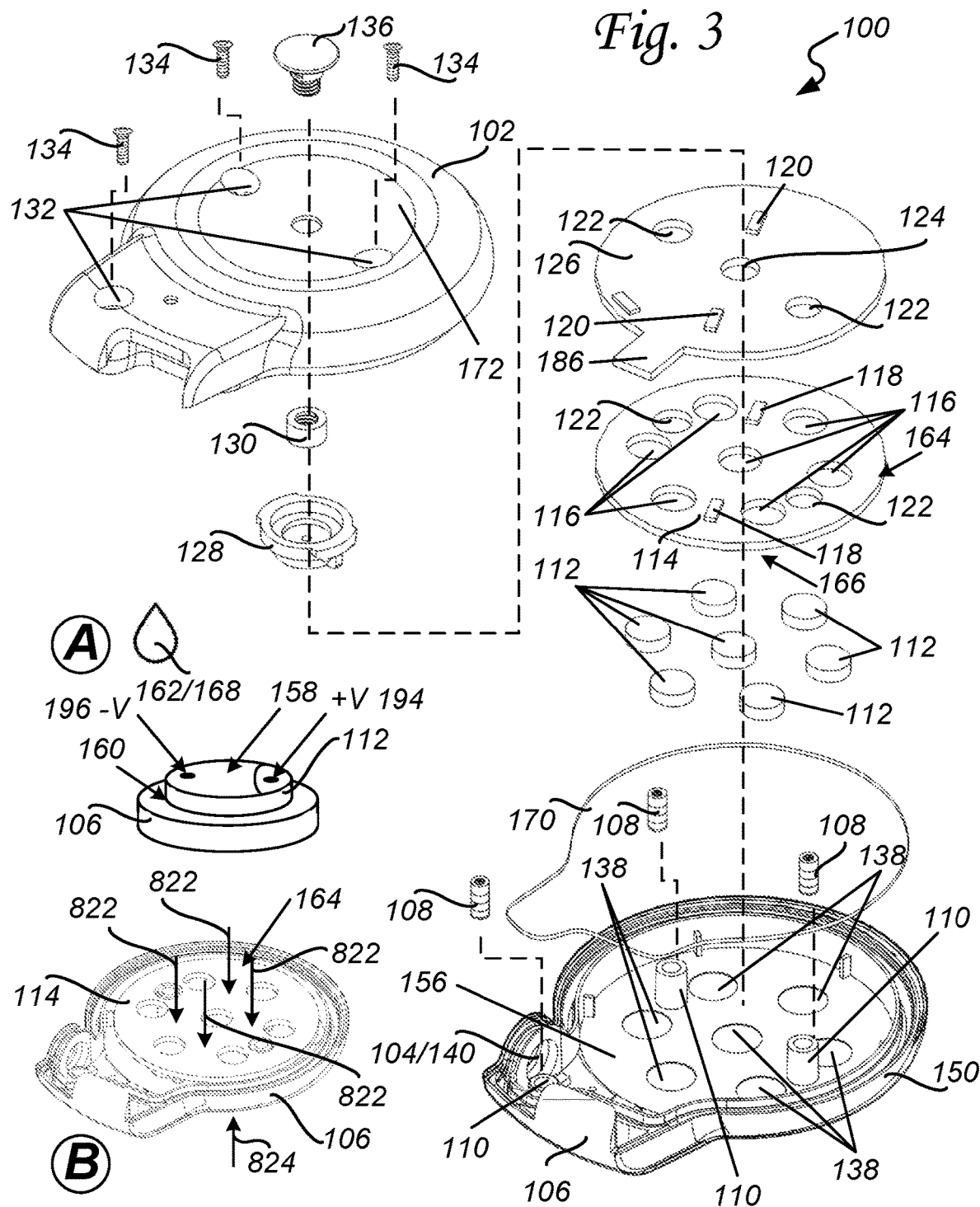
FIG. 3 illustrates one example of an assembly view of an improved fetal heart rate transducer.

Referring to FIG. 3, there is illustrated one example of an assembly view of an improved fetal heart rate transducer 100. In an exemplary embodiment, a top case 102, and a bottom case 106 fasten together. The top case comprises a top case exterior surface 172 and a top case interior surface 174 that is better illustrated in at least FIG. 4. More than one recessed opening 132 is positioned over the top of each of the cupped standoffs 148 and non-cupped standoff 182, which is better illustrated in at least FIG. 4, allowing machine screws 134 which are precision shoulder screws to pass through and be counter-sunk in the top exterior surface 172 when the top case 102 and the bottom case 106 are fastened together. Better illustrated in at least FIG. 31, strain relief 354 and rubber boot 358A/358B secure the cable 350A by way of the cable connector 104/140 hole/cavity to the transducer 100. Rubber boot 358A style is used with transducer 100 and rubber boot 358B style is used with transducer 200.

The bottom case 106 comprises an interior surface 156. The interior surface 156 has de-embossed or raised more than one piezo-electric crystal (PZT) pad 138, and more than one standoff 110. More than one metal insert 108 is molded into place within the standoff 110 as the bottom case 106 is fabricated in the mold with plastic resin. In this regard, an advantage, in the present invention, is that the metal inserts 108/222/224 are not press-fitted creating stress in the standoffs 110 that leads to cracking. Such cracks allow the components to loosen, shift, or vibrate causing misreading FHR and other operational errors. Rather, the metal inserts 108/222/224 are placed in the mold at the time the bottom case 106/204 is fabricated or otherwise molded so that there is no stress with respect to the interface between the metal inserts 108/222/224 and the standoffs 110 eliminating the possibility of stress cracks forming over time.

The improved fetal heart rate transducer 100 further comprises more than one piezo-electric crystal (PZT) disc 112 having a top side 158 and an epoxy side 160. Such PZT disc 112 can be lead zirconate titanate discs or other types and kinds of PZT discs, as may be required and/or desired in a particular embodiment.

In prior transducers, bonding of the PZT discs to the plastic surface becomes weak as the one-part silicone adhesive used develops micro-cracks allowing air pockets and the partially anchored PZT disc movement that gives rise to ultrasound echo signal with Doppler frequency shift that gets translated as a spurious FHR.

In contrast and advantage, in the present invention, PZT disc bonding failures and spurious FHR shortcomings are overcome by utilizing a different PZT bonding approach and epoxy adhesive. In this regard, in an exemplary embodiment, in the fabrication of the improved fetal heart rate transducer 100, each of the PZT disc 112 adheres to the PZT pad 138 as follows; the interior surface 156 and the PZT disc 112 are cleaned with a mild soap solution, rinsed with deionized/distilled water, and air dried. An ultra slow-cure epoxy 162 is mixed and degassed in a vacuum for a degassing time period. In an exemplary embodiment, the ultra slow-cure epoxy 162 can be mixed as four parts of resin to one part hardener, and the degassing time period can be in the range of 15 to 20 minutes.

The manner in which the PZT disc 112 adheres to the PZT pad 138 continues as follows with a drop of the degassed ultra slow-cure epoxy 162 being deposited in the center of the epoxy side 160 of each of the PZT disc 112/218 while the PZT disc 112/218 is resting on a horizontal surface with the epoxy side 160 up, or the PZT pad 138/232 while the bottom case 106/204 is resting on a horizontal surface. The drop of ultra slow-cure epoxy 162 is then allowed to self-level for a self-leveling time period. In an exemplary embodiment, the self-leveling time period can be in the range of 15 to 20 minutes.

In the present invention, the term "self-leveling" is intended to mean the process of allowing gravity to act on a liquid medium and/or a weight on a liquid medium to evenly distribute the liquid medium across a surface. In this regard, the liquid can be a drop of epoxy such as the slow-cure epoxy 168 and the ultra slow-cure epoxy 162 that are allowed to self-level under the force of gravity or under the weight of a PZT disc 112/218 placed on top of the epoxy 162/168. In operation, the epoxy is dispersed in a thin, smooth, horizontal, degassed, and uniformly thick manner, and objects placed on the epoxy 162/168 such as the PZT disc 112/218 self-level as well in a horizontal manner.

The manner in which the PZT disc 112 adheres to the PZT pad 138 continues as follows, as illustrated in at least FIG. 3, reference 'A', by placing the epoxy side 160 of each of the PZT disc 112 on each of the PZT pad 138 while the bottom case 106 is resting on a horizontal surface. The PZT disc 112 and the bottom case 106 assembly are then allowed to self-level under the weight of the PZT disc 112 and cure for a cure time period. In an exemplary embodiment, the cure time period can be in the range of a minimum of 68 hours.

Prior transducers that bond the frontend PCB 114 to the plastic case 106 suffer shortcomings of bond failure between the plastic case and the frontend PCB that results in the frontend PCB coming loose from the plastic partially or entirely. In both cases, frontend PCB vibration or worse complete and continuous movement gives rise to an ultrasound echo signal with Doppler frequency shift that gets translated as a spurious FHR. When frontend PCB 114 becomes partially or completely loose, the backend PCB (main CPU PCB) 126 also vibrates or intermittently moves resulting Doppler shift in reflected echo signal that translates to spurious FHR, and in addition, various electrical signal issues such as noise are caused as the electrical connections through two header pin connectors 118/120 with frontend PCB 114 go through make-break cycles.

In contrast and advantage, in the present invention, the frontend PCB bonding failures and spurious FHR shortcomings are overcome by utilizing a different frontend PCB bonding approach. In this regard, in an exemplary embodiment, the improved fetal heart rate transducer 100 further comprises a frontend printed circuit board (PCB) 114 that has a PCB top side 164 and a PCB epoxy side 166. Each of the PZT discs 112 electrically interconnects with and is operationally related to the frontend PCB 114.

In an exemplary embodiment, in the fabrication of the improved fetal heart rate transducer 100, the frontend PCB 114 adheres to the interior surface 156 of the bottom case 106 as follows, the PCB epoxy side 166 of the frontend PCB 114 is cleaned with isopropyl alcohol, and air dry. A slow-cure epoxy 168 is mixed and degassed in a vacuum for a degassing time period. In an exemplary embodiment, the slow-cure epoxy 168 can be mixed as two parts resin to one part hardener, and the degassing time period can be in the range of 8 to 10 minutes.

The manner in which the frontend PCB 114 adheres to the interior surface 156 of the bottom case 106 continues as follows by coating the PCB epoxy side 166 of the frontend PCB 114 with a uniform layer of the slow-cure epoxy 168 while the frontend PCB 114 is resting on a horizontal surface with the PCB epoxy side 166 up. The uniform epoxy layer is allowed to self-level for a self-leveling time period. In an exemplary embodiment, the self-leveling time period can be in the range of 10 to 15 minutes. The frontend PCB 114 is then placed in position with the PCB epoxy side 166 in contact with the interior surface 156 of the bottom case 106. The frontend PCB 114 is then allowed to self-level under its weight for a self-leveling time period. In an exemplary embodiment, the frontend PCB 114 self-leveling time period can be in the range of 10 to 15 minutes.

The manner in which the frontend PCB 114 adheres to the interior surface 156 of the bottom case 106 continues as follows, as illustrated in at least FIG. 3 reference 'B', by clamping 822/824, for a cure time, the frontend PCB 114 and the bottom case 106 at more than one pressure point 822. The pressure points 822 are symmetrically located on the surface of the top side 164 of the frontend PCB 114. In an exemplary embodiment, the cure time can be in the range of 24 to 36 hours.

Transducer failure, intermittent operation, and spurious FHR in prior transducers are often caused by bonding shortcomings such as weak, failed, cracked, airgap ridden, and/or uneven bonding thickness between the PZT discs 112/218 and if bonded to the plastic case the frontend PCB 114. Additionally, transducer failure, intermittent operation, and spurious FHR in prior transducers can be caused by press-fitting metal inserts into plastic standoffs that eventually cause the standoffs to crack creating vibration and motion of the backend PCB 126/216, top case 102/210A/210B, and other internal parts.

To illustrate this point, first consider normal transducer operation where the transducer is mechanically stable, and absent any component vibrations. The PZT disc emits ultrasound waves from both disc faces, the top surface face and the bottom surface face. The bottom surface face of the disc when perfectly epoxied to the plastic substrate through which the ultrasound wave of 1 MHz frequency travels out of the transducer 100.

Inside the transducer, a backend PCB 126 is installed about 2.8 mm distance above the PZT disc top surface face, and orientated in a parallel plane (transverse to the emitted ultrasound wave travel). In this example, since the transducer 100 is mechanically stable, and absent any component vibrations there is no movement of the backend PCB 126, top plastic case 102, or the PZT disc 112. While the backend PCB 126 and the top case 102 do reflect ultrasound waves, the reflected frequency perceived will be the same as 1 MHz that was transmitted by the PZT disc 112. Allowing only the reflected frequency from the bottom surface face 198 that is coupled to the patient 502 to vary engendering correct transducer operation and readings.

Now consider abnormal transducer operation, where the transducer is mechanically unstable, in that the adhesive layer on one of the PZT discs is failing, acting like a rubber cushion, allowing the PZT disc to vibrate up-down with 50 micrometers (0.05 mm) amplitude just for 100 milliseconds (0.1 sec). In this case, the reflected 1 MHz wavefront from the stationary backend PCB will be perceived as a little higher frequency than 1 MHz when the PZT disc moves towards the backend PCB and a little lower frequency than 1 MHZ when the PZT disc moves away from the backend PCB. The frequency change perceived/detected by the PZT disc will be proportional to the velocity of the PZT disc itself (as an observer in receiving mode) in either direction. As an example, if the PZT disc velocity was 1 micrometer per microsecond when it moved towards the main CPU PCB (backend PCB 126), it would measure the reflected wave from stationary PCB as frequency 1.002915 MHz (2.915 kHz more than the originally transmitted frequency of 1 MHz). If the disc moves away from the PCB (towards the bottom case) with the same velocity, the reflected wave from the stationary PCB would be measured as a frequency of 0.997093 MHz which is lower by 2.906 kHz as compared to the originally transmitted ultrasound pulse of 1 MHz. In this example, for purposes of calculations, the velocity of sound in the air medium (between the PZT disc and the backend PCB) is taken as 343 m/s at 20° C.

When the ultrasound transducer is strapped to the abdomen of the patient to monitor the fetus, the PZT discs receive useful echo signal (at the bottom surface face 198/256 of the transducer) from the fetal heart (that is beating) with Doppler frequency shift proportional to the heart movement as well as from the internal parts (on the top surface face side of PZT disc), including from the backend PCB, top case, metal threaded inserts and any of these internal components that make spurious/intermittent movement in micrometers, making the Doppler shift echo signal results very unreliable for FHR detection.

The error in FHR detection worsens if one or more PZT discs are loose as the loose disc acts as a moving observer/receiver and echo signals from perfectly stationary targets (PCB, top case, metal inserts) contribute to the Doppler shift frequency proportional to the PZT disc movement. Table 820 in FIG. 30 illustrates the Doppler equations for the frequency shift calculation. The third and fourth rows in the table represent the condition where the backend PCB and top case are stationary and a PZT disc is intermittently moving, acting as an observer.

During a patient's respiration cycle, the abdominal belt 364 experiences slight pressure changes and if there is a movement of the PZT disc, frontend PCB, backend PCB, top case, or other components, such movement translates into a spurious reading of the FHR. The movement of components can also be facilitated by the use of self-tapping screws that loosen over a short span of time. Any unintended moving object/target (continuously or intermittently) directly in the path of the ultrasound beam on either side of PZT discs (bottom side towards fetus, top side internal to transducer head) produces a Doppler shift echo proportional to the velocity of the moving object/target and gets translated into spurious FHR readings even when there is no fetus present.

An advantage, in the present invention, to overcome these unintended intermittent/spurious FHR readings is the use of an approach for bonding the PZT discs 112/218 and frontend PCB 114 using a two-part ultra slow-curing epoxy 162 on the PZT discs 112/218 and a two-part slow-curing epoxy 168 on the frontend PCB 114 to achieve the bond strength necessary to withstand test impact forces. Such, impact forces are generated in a drop test by dropping the transducer from a height of 22 feet onto a hard concrete floor.

During laboratory testing, of the bonding materials and approach in the present invention, and utilizing the 22-foot drop test mentioned above we found that the plastic parts, connectors, top case, or bottom case, were suspectable to damage but the PZT discs and frontend PCB bonding remained intact. In other words, for the PZT discs and the frontend PCB to be separated from the transducer bottom case surface, the plastic substrate should first have to be destroyed physically, which means the bonding is rated for use for the lifetime of the transducer.

Figure 4:
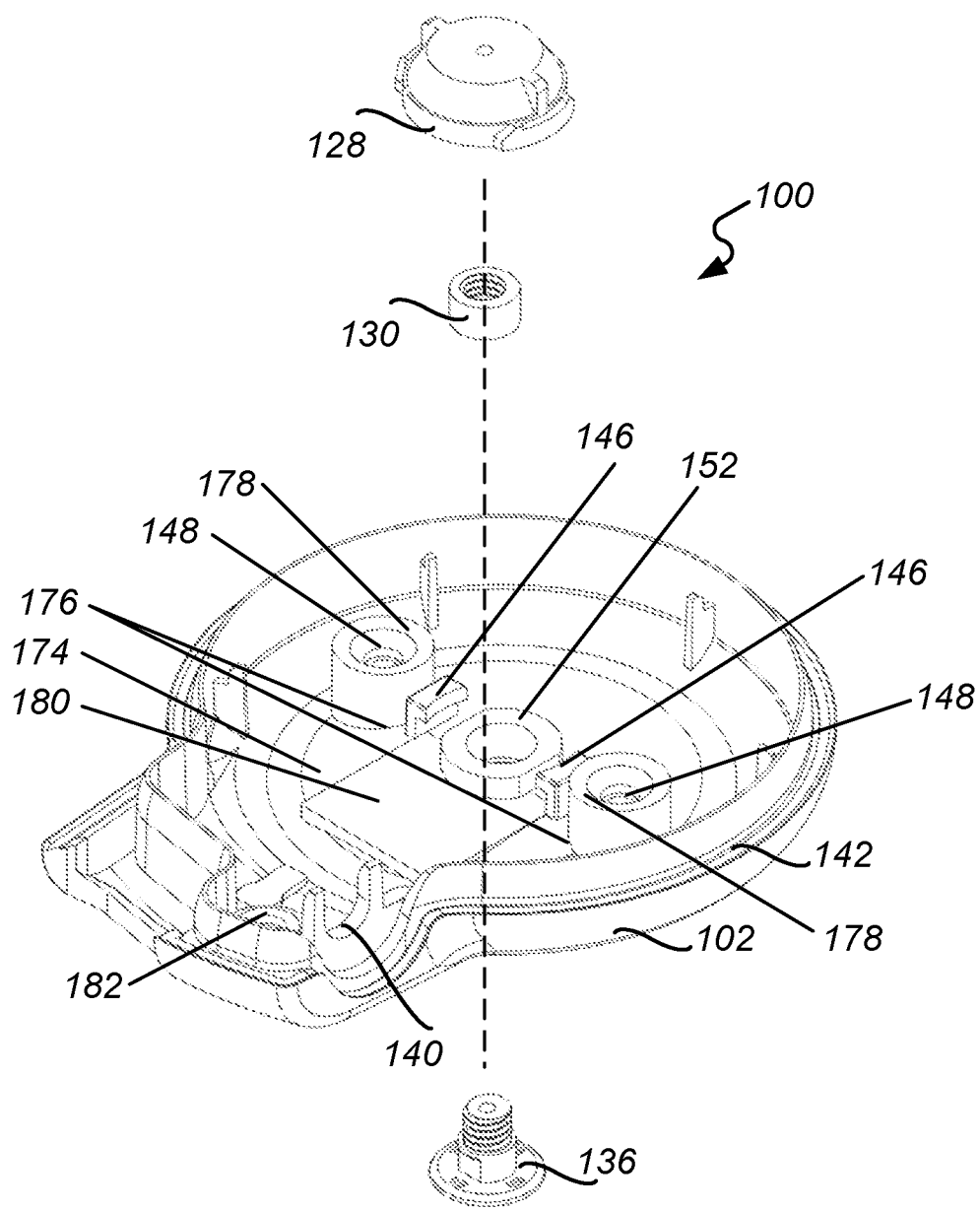
FIG. 4 illustrates one example of a top case assembly view of an improved fetal heart rate transducer.

In an exemplary embodiment and with reference to FIGS. 3 and 4, where FIG. 4 illustrates one example of a top case assembly view of the improved fetal heart rate transducer 100, the top case 102 comprises a top case top side 172, a top case interior surface 174, a top groove 142, a button fastener retainer 152, an inclined plane 180, more than one retaining clip 146, and more than one cupped standoff 148. The cupped standoffs 148 comprise a cupped standoff bottom 176 that is integrally formed with the top case interior surface 174, and a cupped standoff top 178 that has a raised ridge edge around the circumference of the cupped standoff 148 top creating a cavity that is sized to interconnect with the standoff 110 on the bottom surface 106 after passing through the frontend PCB 114 and the backend PCB 126 in a manner that allows the raised ridge edge 178 to contact and immobilize the backend PCB 126 from movement when the top case 102 and the bottom case 106 are fastened together.

In an exemplary embodiment, a threaded button fastener 130 can be molded into the button fastener retainer 152 from the top case interior surface 174 side of the top case 102. A threaded button 136 can be inserted through the top case 102 top side into the threaded button fastener and tightened, securing the threaded button to the top case of the top case 172. A cover 128 covers the button fastener retainer 152 and the threaded button fastener 130. The cover is secured under the retaining clip 146 in a manner that the inclined plane 180 applies force to cover 128 holding it from displacement from the retaining clip 146. A gasket 170 can be fitted into the top groove 142 and a bottom groove 150 forming a seal between the top case 102 and the bottom case 106 when fastened together. The bottom case 106 comprises the bottom groove 150.

Referring to FIGS. 4-8 are illustrated examples of an improved fetal heart rate transducer 100. FIG. 5 illustrates one example of a bottom case 106 where reference 'A' is an exterior surface view and reference 'B' is an interior surface view. In an exemplary embodiment, the height of a raised island pad 184 can be selected so that a PCB tab 186 that is part of the backend PCB 126 (see at least FIG. 2) can rest on island pad 184 limiting backend PCB 126 motion/vibration when the transducer 100 is assembled.

Referring to FIG. 6 there is illustrated one example of a top case 102 view where reference 'A' is an exterior surface view and reference 'B' is an interior surface view. The top case comprises a top case exterior surface 172 and a top case interior surface 174. More than one recessed opening 132 is positioned over the top of each of the cupped standoffs 148 and non-cupped standoff 182 allowing machine screws 134 that are precision shoulder screws with longer thread length than used in prior transducers to pass through and be counter-sunk to the top exterior surface 172 when the top case 102 and the bottom case 106 are fastened together.

Figure 9:
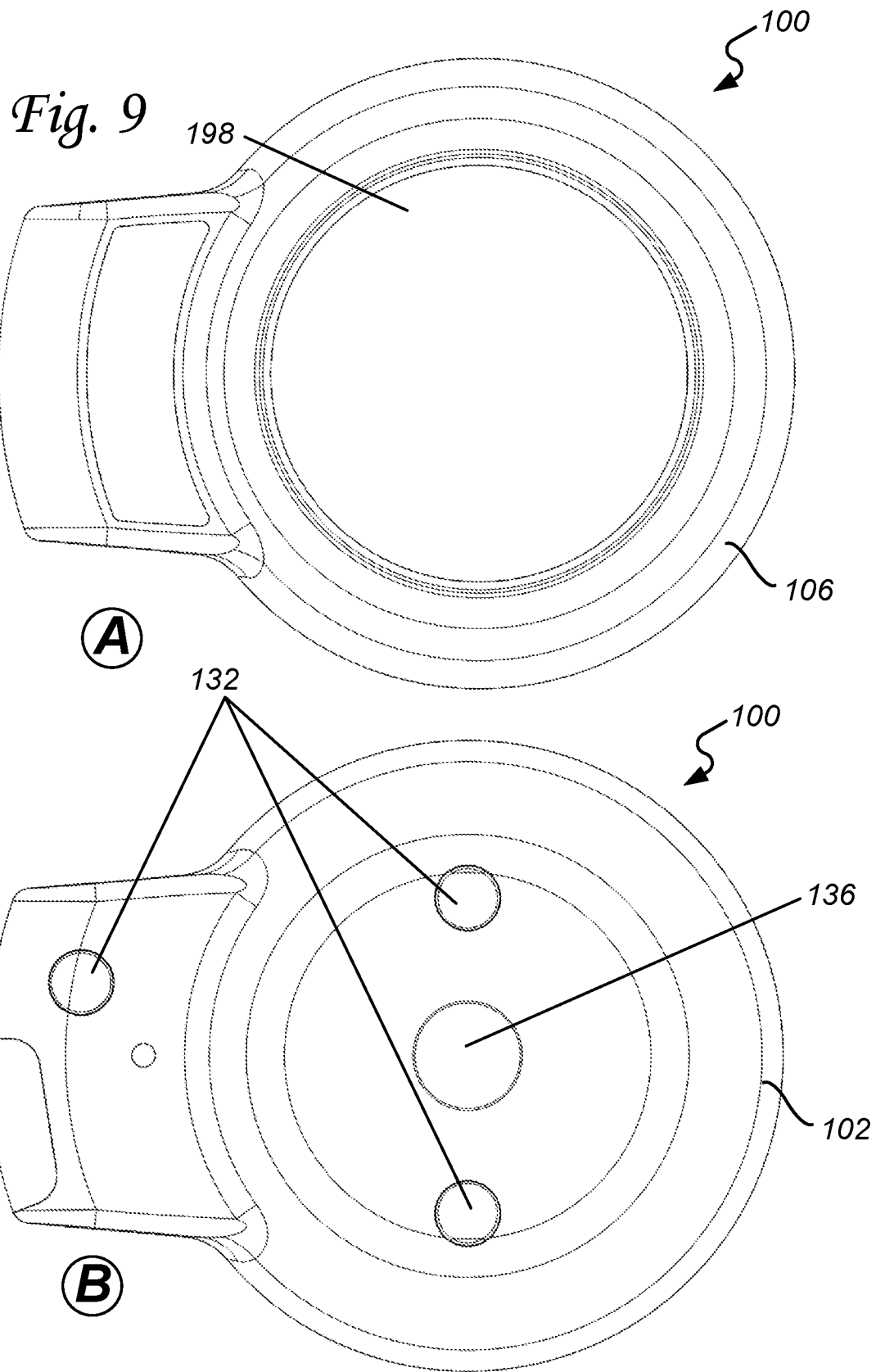

Referring to FIG. 7 reference 'A' there is illustrated as one example of a left side view of the assembled improved fetal heart rate transducer 100, and reference 'B' is a right side view of the improved fetal heart rate transducer 100. FIG. 8 reference 'A' illustrates one example of a back side view of improved fetal heart rate transducer 100, and reference 'B' illustrates one example of a front side view of improved fetal heart rate transducer 100. FIG. 9 reference 'A' illustrated one example of a bottom side view of improved fetal heart rate transducer 100, and reference 'B' illustrates one example of a top side view of improved fetal heart rate transducer 100.

Referring to FIG. 10, there is illustrated one example of a perspective view of an improved fetal heart rate transducer 200 that comprises more than one belt slot 202. In an exemplary embodiment, reference 'A' is an exterior surface view of the top side of the improved fetal heart rate transducer 200, and reference 'B' is the exterior surface view of the bottom side of the improved fetal heart rate transducer 200. In operation, a belt 364 can be passed through belt slot 202 to secure the improved fetal heart rate transducer 200 to patient 502.

Figure 12:
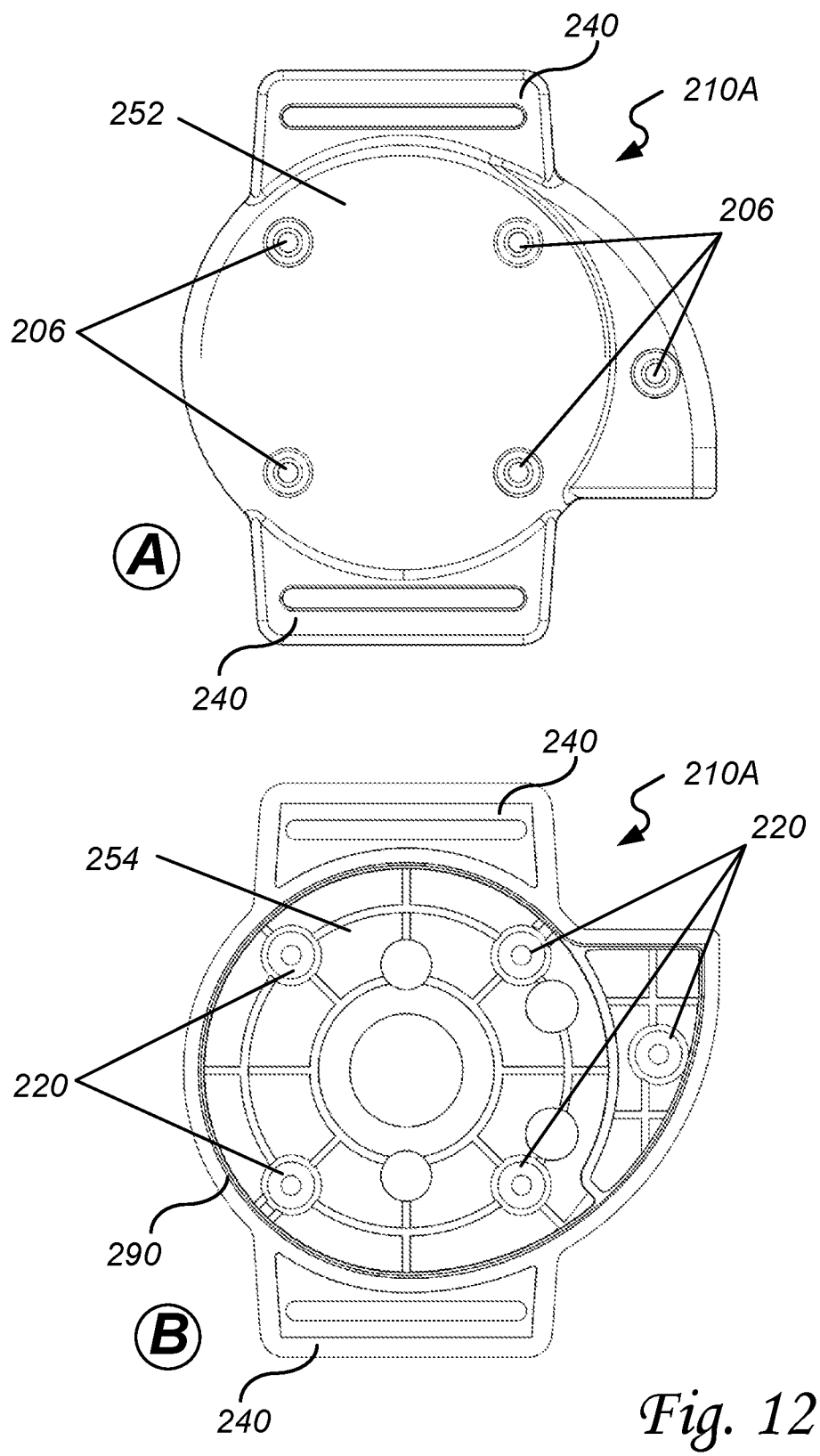

The top case comprises a top case exterior surface 252 and a top case interior surface 254 (as better illustrated in at least FIG. 12. More than one recessed opening 206 is positioned over the top of each of the top case standoffs 220 allowing machine screws 250 to pass through and be counter-sunk to the top exterior surface 252 when the top case 210A or 210B and the bottom case 204 are fastened together. With regards to attaching to the belt 364 and positioning and securing the improved fetal heart rate transducer 200 around patient 502, top case 210A has belt slots, and top case 210B has button 212. Both tops 210A and 210B cases can be used interchangeably in the present invention. Rubber boot 358A style is used with transducer 100 and rubber boot 358B style is used with transducer 200.

In an exemplary embodiment, the top case 210A/210B and the bottom case 204 can be manufactured from plastic, or other suitable materials.

Figure 11:
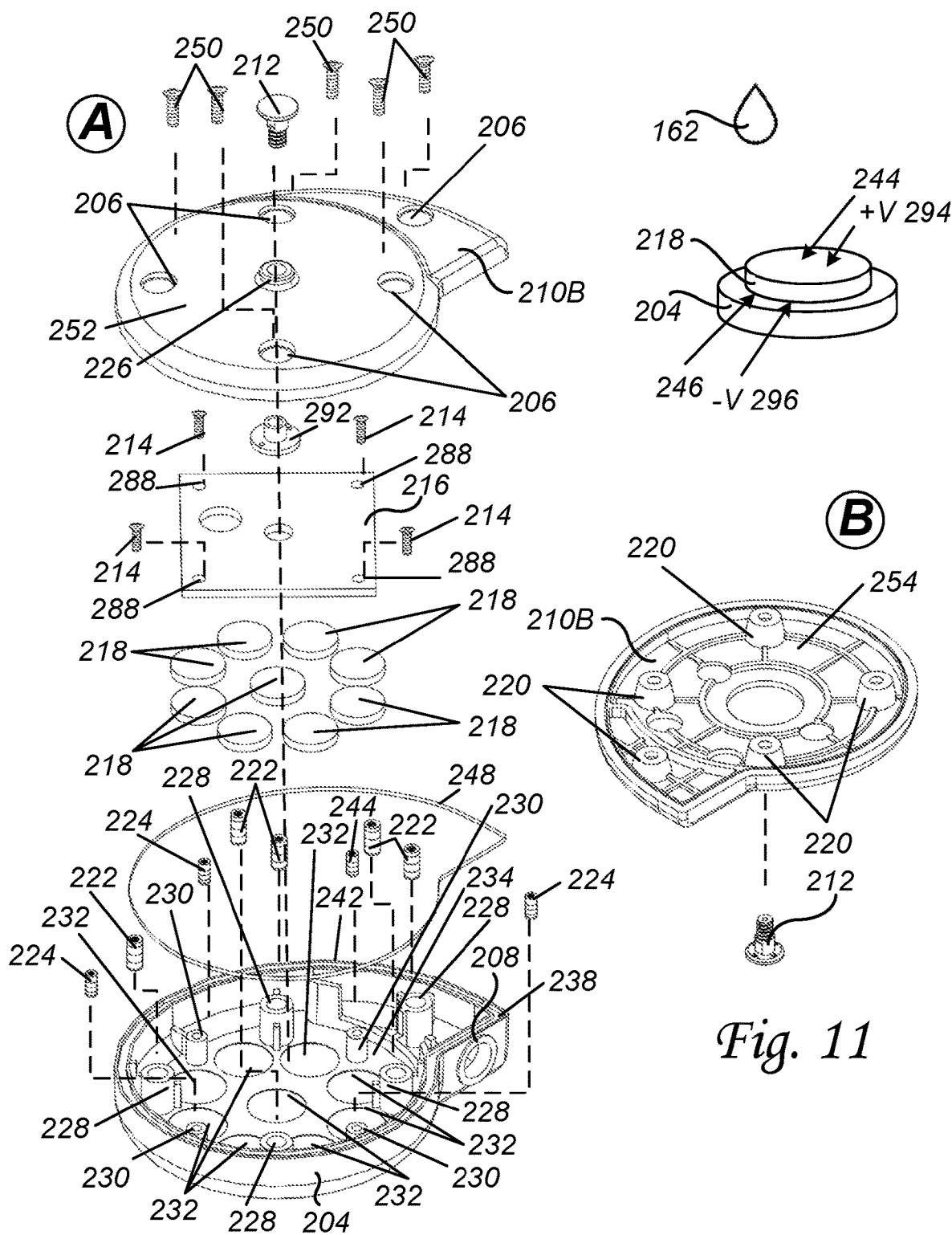
FIG. 11 illustrates one example of an assembly view of an improved fetal heart rate transducer.

Referring to FIG. 11, there is illustrated one example of an assembly view of an improved fetal heart rate transducer 200. In an exemplary embodiment, a top case 210A or 210B, and a bottom case 204 fasten together. As better illustrated in at least FIG. 12, the top case 210A/210B comprises a top case exterior surface 252 and a top case interior surface 254. More than one recessed opening 206 is positioned over the top of each of the top case standoffs 220 allowing machine screws 250 to pass through and be counter-sunk in the top exterior surface 252 when the top case 210A/210B and the bottom case 204 are fastened together.

The bottom case 204 comprises an interior surface 234. The interior surface 234 has de-embossed or raised more than one piezo-electric crystal (PZT) pad 232, and more than one standoff 228/230. More than one metal insert 222/224 is molded into place within the standoff 228/230 as the bottom case 204 is fabricated in the mold with plastic resin. In this regard, an advantage, in the present invention, is that the metal inserts are not press-fitted into the standoffs 228/230 creating stress in the standoffs 228/230 that leads to cracking in the standoffs 228/230. Such cracks allow the components inside to loosen, shift or move with vibration and adjustment that cause misreading (FHR) and other operational errors. Rather, the metal inserts 222/224 are placed in the mold at the time the bottom case 204 is fabricated or otherwise molded so that there is no stress with respect to the interface between the metal inserts 222/224 and the standoffs 228/230 eliminating the possibility of stress cracks forming over time.

In prior transducers, only three standoffs with no inserts, using self-tapping screws instead, were utilized leaving one corner of the frontend PCB 216 loose to vibrate causing FHR errors. In contrast and advantage, in the present invention, four standoffs 230 have metal inserts 244 molded in at the time the bottom case 204 is formed. This approach secures each of the four corners of the frontend PCB 216 with machine screws 214 into the metal inserts 244 that hold the frontend PCB 216 from vibrating at each corner without cracking the standoffs 230.

The improved fetal heart rate transducer 200 further comprises more than one PZT disc 218 having a top side 244 and an epoxy side 246. Such PZT disc 218 can be lead zirconate titanate discs or other types and kinds of PZT discs, as may be required and/or desired in a particular embodiment.

In an exemplary embodiment, in the fabrication of the improved fetal heart rate transducer 200, each of the PZT disc 218 adheres to the PZT pad 232 as follows the interior surface 234 and the PZT disc 218 are cleaned with a mild soap solution, rinsed with deionized/distilled water, and air dried. An ultra slow-cure epoxy 162 is mixed and degassed in a vacuum for a degassing time period. In an exemplary embodiment, the ultra slow-cure epoxy 162 can be mixed as four parts of resin to one part hardener, and the degassing time period can be in the range of 15 to 20 minutes.

The manner in which the PZT disc 218 adheres to the PZT pad continues as follows with a drop of the ultra slow-cure epoxy 162 being deposited in the center of the epoxy side 246 of each of the PZT disc 218 while the PZT disc 218 is resting on a horizontal surface with the epoxy side 246 up, or the PZT pad 232 while the bottom case 204 is resting on a horizontal surface. The drop of ultra slow-cure epoxy 162 is then allowed to self-level for a self-leveling time period. In an exemplary embodiment, the self-leveling time period can be in the range of 15 to 20 minutes.

In an exemplary embodiment, PZT Pads 232 can have a small cutout or notch at the perimeter to accommodate PZT disc types where one of the wire electrodes is bonded to the side epoxy side 246. In this regard, the small cutout allows the wire to egress the PZT pad 232 so the PZT disc 218 can sit flat on the PZT pad 232 surfaces.

The manner in which the PZT disc 218 adheres to the PZT pad 232 continues as follows by placing the epoxy side 246 of each of the PZT disc 218 on each of the PZT pad 232 while the bottom case 204 is resting on a horizontal surface. The PZT disc 218 and the bottom case 204 assembly are then allowed to self-level under the weight of the PZT disc 218 and cure for a cure time period. In an exemplary embodiment, the cure time period can be in the range of a minimum of 68 hours.

The improved fetal heart rate transducer 200 further comprises a frontend printed circuit board (PCB) 216. Each of the PZT disc 218 interconnects with and is operationally related to the frontend PCB 216.

In an exemplary embodiment, in the fabrication of the improved fetal heart rate transducer 200, the frontend PCB 216 comprises PCB mounting holes 288 that align with the standoffs 230. Machine screws 214 are placed through the PCB mounting holes 288 and secured into the metal inserts 224 that are formed into the standoffs 230 securing the frontend PCB 216 to the bottom case 204 using machine screws.

In an exemplary embodiment, and with reference to FIGS. 11 and 12, where FIG. 12 illustrates one example of a top case assembly view of the improved fetal heart rate transducer 200, the top case 210A comprises a top case top side 252, a top case interior surface 254, a top perimeter edge 290, a button fastener retainer 292 molded into the top case 210B, and more than one top case standoff 220.

In an exemplary embodiment, the top case 210A comprises more than one belt slot 240 through which a belt 364 can be secured. A gasket 248 can be fitted into a bottom groove 238 that engages the top perimeter edge 290 forming a seal between the top case 210A/210B and the bottom case 204 when fastened together. The bottom case 204 comprises the bottom groove 238.

In an exemplary embodiment, internal cavity surfaces 254/234 of top case 210A/210B and bottom case 204 of transducer 200 can be coated with electrically conductive material to form a Faraday cage shield for EMI. In prior transducers, over a period of time, the conductive layer oxidizes and peels off and loose flakes become the source of spurious FHR. An advantage, in the present invention, is that by utilizing and improved method to spray plating catalyst (Autocatalytic Plating process) onto the areas of the internal cavity surface 254/234 bonding is improved and spurious FHR caused by flaking is eliminated. In operation, paint masks are used to control the location of where the catalyst is dispersed on the internal cavity surfaces 254/234. In this regard, PZT pads 232 for PZT discs 232 are masked so that catalyst is not deposited on the PZT pad 232 surface. The chemical make-up of the catalyst draws copper metal out of the plating solution, and deposits copper uniformly onto the catalyzed area. It is followed by electroless copper plating and finally, electroless nickel plating is applied to protect the copper from corrosion and abrasion.

Figure 13:
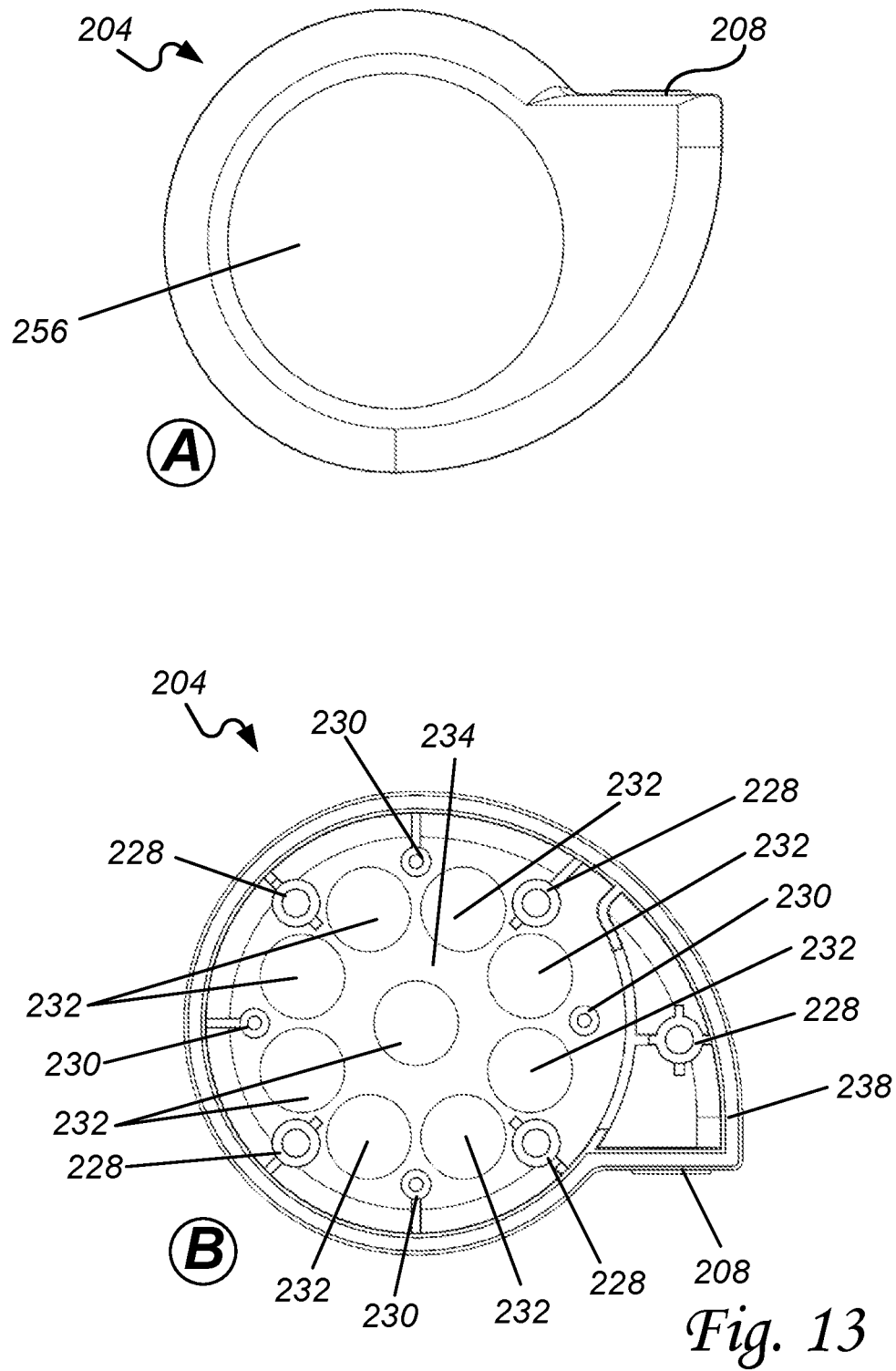

Referring to FIGS. 12-21, there are illustrated examples of an improved fetal heart rate transducer 200. FIG. 12 illustrates in reference 'A' an exterior surface 252 views of a top case 210A that has belt slots 240, and in reference 'B' an interior surface 254 of a top case 210A that has belt slots 240. FIG. 13 illustrates in reference 'A' an exterior surface 256 of a bottom case 204, and an interior surface 234 of a bottom case.

Referring to FIG. 14, there is illustrated in reference 'A' a left side view of the improved fetal heart rate transducer 200, and in reference 'B' a right side view of the improved fetal heart rate transducer 200. The bottom case 204 comprises a cable connector 208 hole/cavity for cable-strain relief installation. The cable connector 208 securing one end of cable 330 connects the improved fetal heart rate transducer 100/200 to the fetal monitor 500.

Referring to FIG. 15 reference 'A' illustrates one example of a front side view of the improved fetal heart rate transducer 100, and reference 'B' illustrates one example of a back side view of the improved fetal heart rate transducer 200.

Figure 16:
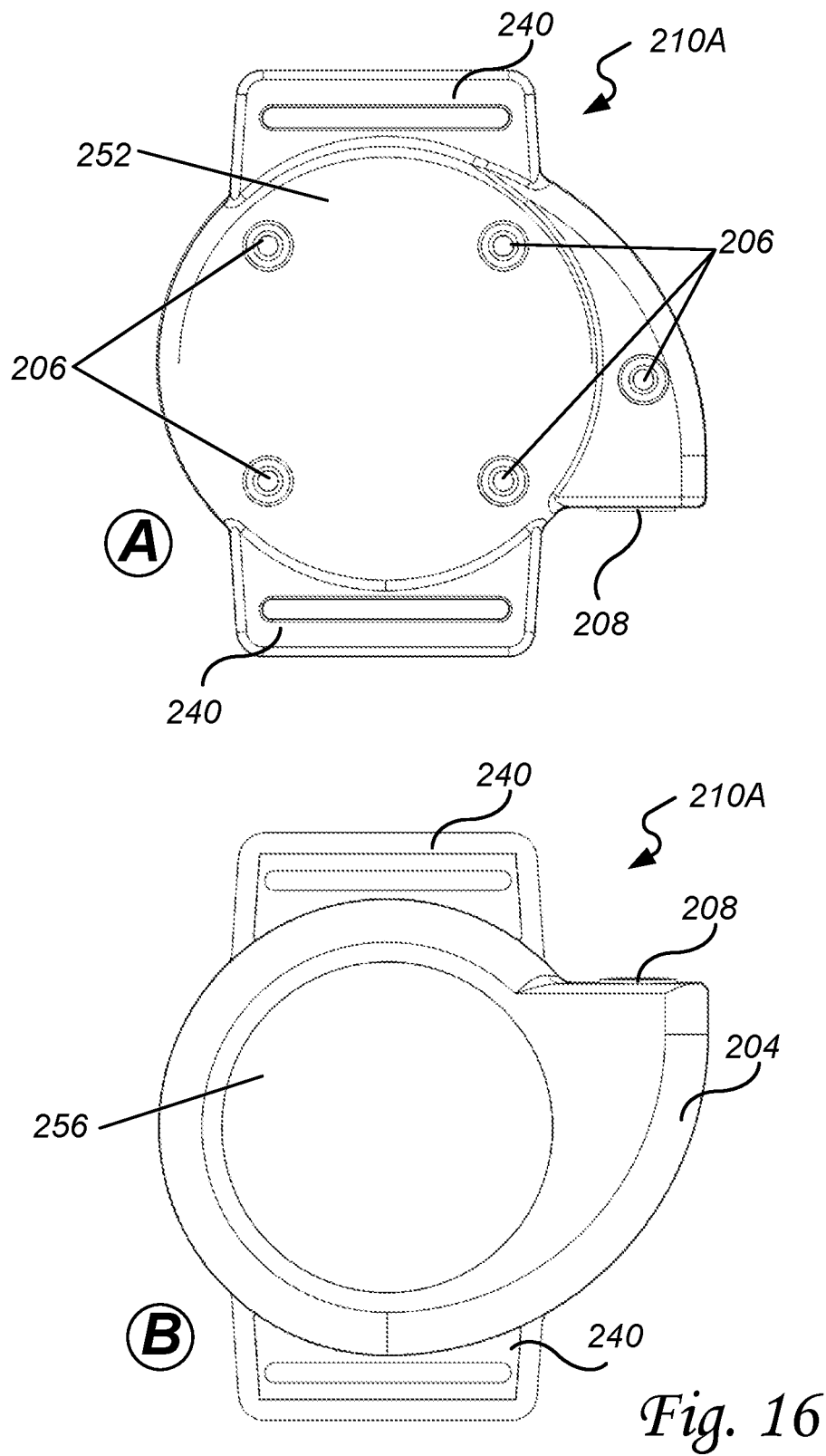

Referring to FIG. 16 reference 'A' illustrated one example of a top side view of the improved fetal heart rate transducer 200 with belt slots 240, and reference 'B' illustrates one example of a bottom side view of the improved fetal heart rate transducer 200.

Referring to FIG. 17, there is illustrated one example of a perspective view of an improved fetal heart rate transducer 200 that has button 212. In an exemplary embodiment, reference 'A' is an exterior surface 252 view of the top side of the improved fetal heart rate transducer 200, and reference 'B' is the exterior surface 256 view of the bottom side of the improved fetal heart rate transducer 200.

Figure 18:
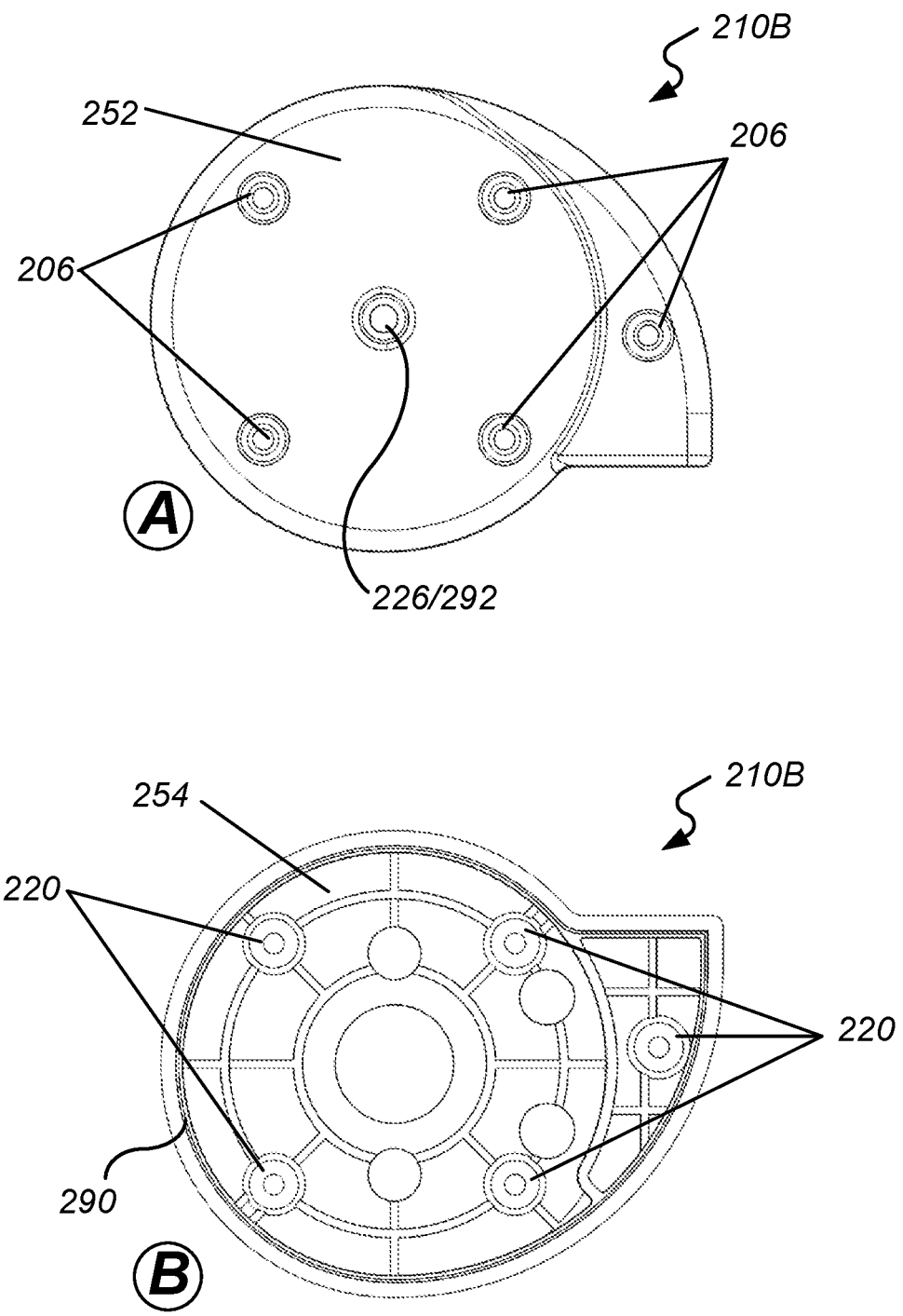

Referring to FIG. 18, there is illustrated in reference 'A' one example of the top surface 252 of a top case 210B having a button fastener retainer 226, and in reference 13' the bottom surface 254 of the top case 210B. In an exemplary embodiment, the top case 210B comprises a top case exterior surface 252 and a top case interior surface 254. More than one recessed opening 206 is positioned over the top of each of the top case standoffs 220 allowing machine screws 250 to pass through and be counter-sunk to the top exterior surface 252 when the top case 210A or 210B and the bottom case 204 are fastened together. With regards to attaching to the belt 364 and positioning and securing the improved fetal heart rate transducer 200 around patient 502, top case 210A has belt slots, and top case 210B has button 212. Both tops 210A and 210B cases can be used interchangeably in the present invention.

Figure 19:
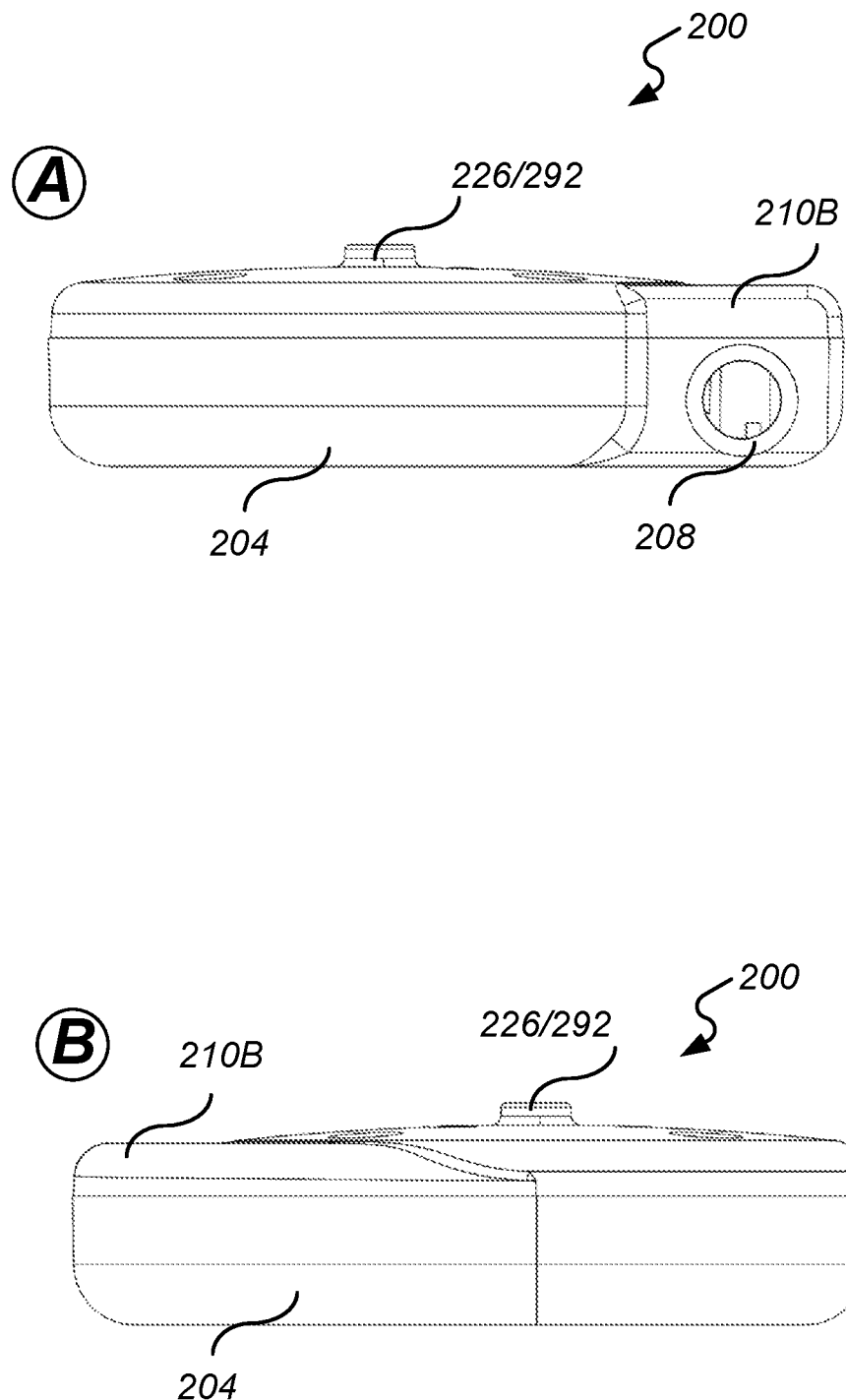

Referring to FIG. 19, there is illustrated in reference 'A' one example of a left side view wherein the top case 210B is configured with a button fastener retainer 226, and in reference 'B' the bottom surface 254 of the top case 210B. FIG. 20 illustrates in reference 'A' one example of a front side view wherein the top case 210B is configured with a button fastener retainer 226 with molded in button fastener retainer 292, and in reference 'B' a back side surface 254 of the top case 210B. FIG. 21 illustrates in reference 'A' one example of a top 210B side view wherein the top case 210B is configured with a button fastener retainer 226 with molded in button fastener retainer 292, and in reference 'B' a bottom 204 side view.

In an exemplary embodiment, button fastener retainer 226 with molded in button fastener retainer 292 does not get knocked off in drop tests from 18 ft height to concrete floor and hence more likely to last the lifetime of the transducer 200 as it can only be taken off if the top case 210B is physically destroyed.

In an exemplary embodiment, the improved fetal heart rate transducer 200, the top case 210A comprises a top case top side 252, a top case interior surface 254, a top perimeter edge 290, a button fastener retainer 226 with molded in insert 292 molded into the top case 210B, and more than one top case standoff 220.

In an exemplary embodiment, a threaded button fastener 212 can be inserted into the button fastener insert 292 and tightened securing the threaded button to the top case 204. A gasket 248 can be fitted into a bottom groove 238 that engages the top perimeter edge 290 forming a seal between the top case 210A/210B and the bottom case 204 when fastened together. The bottom case 204 comprises the bottom groove 238.

Figure 22:
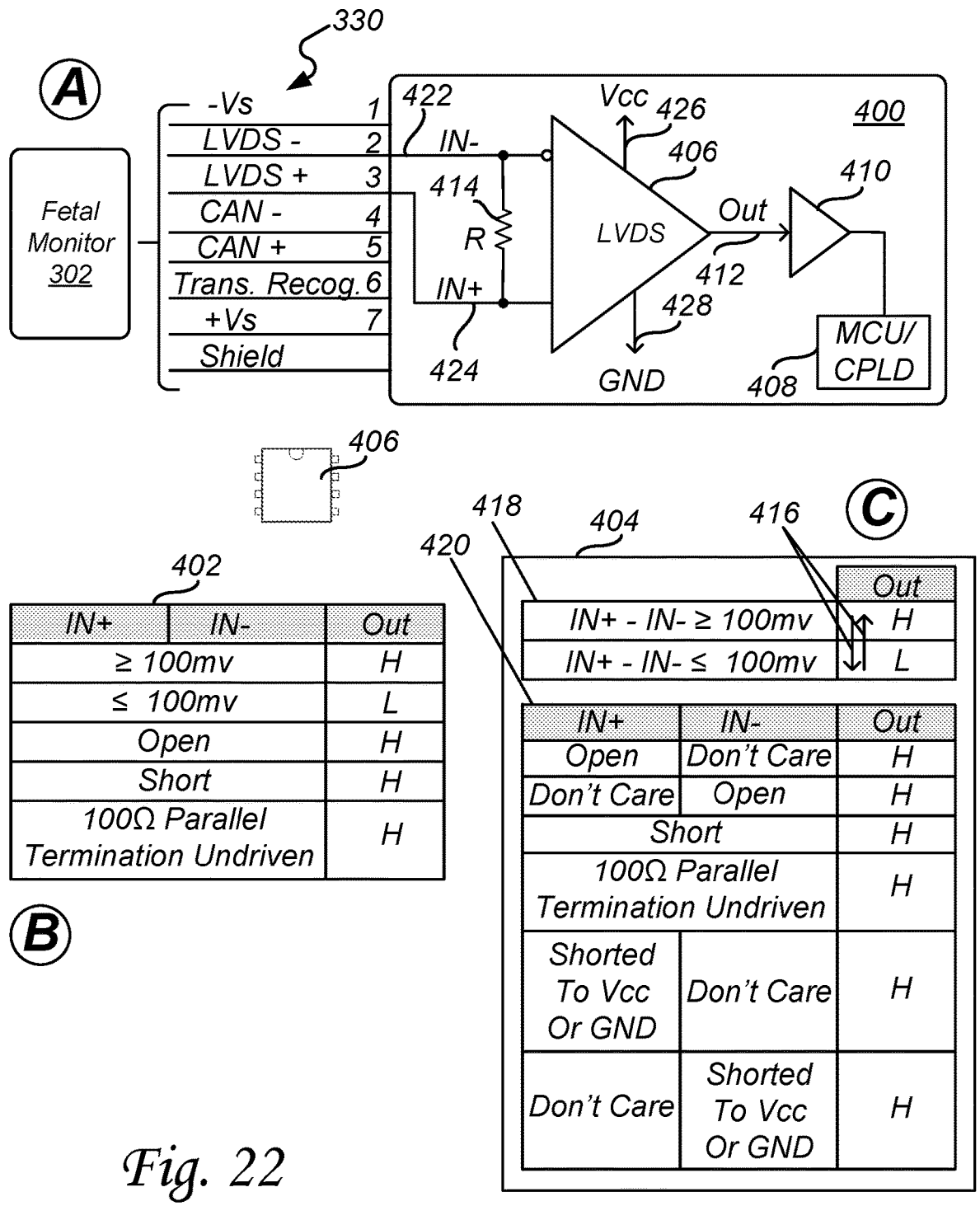
FIG. 22 illustrates one example of a low-voltage differential signal receiver circuit and logic state tables.

Referring to FIG. 22, there is illustrated one example of an electronic control system 400 which is part of the backend main CPU PCB 126 that comprises a low-voltage differential signal (LVDS) receiver circuit 406 and logic state tables. An advantage, in the present invention, is the operation of an electronic control system 400 that comprises the LVDS receiver circuit 406. In this regard and in contrast to the present invention, prior transducers that process the ultrasound signal inside the transducer rather than the fetal monitor, do so based on the state table shown in reference 'B'. As such, these types of prior transducers generate distorted and noisy outputs when a cable wire makes intermittent connections or is broken which causes spurious FHR readings even when there is no patient.

With reference to the seven-conductor (plus the shield) cable 330 illustrated in at least FIG. 22, if any of the five conductors on pins 1, 4, 5, 6, or 7, breaks (electrically open) then the transducer completely stops working but if one of the remaining two conductor connector pins 2 or 3 (LVDS +/−) breaks (electrically open) then the transducer becomes noisy and gives spurious FHR readings. These two conductors (pins 2 and 3) carry a 1 MHz reference signal from the fetal monitor to the transducer head that is processed through the LVDS receiver chip on the backend PCB. In an exemplary embodiment, pin 1 is −Vs, pin 2 is LVDS −, pin 3 is LVDS +, pin 4 is controller area network (CAN) Bus −, pin 5 is CAN Bus +, pin 6 is Transducer Recognition, pin 7 is +Vs, and cable shield is connected to earth ground on the fetal monitor connection end of the cable 330.

The present invention overcomes this shortcoming by providing a failsafe LVDS circuit 406 that is encoded to operate based on the state table in reference 'C'. In an exemplary embodiment and in contrast to prior transducers, in the present invention, the improved LVDS receiver chip 406 has a failsafe circuit and encoded state table operation that outputs a logic high signal (H) state that is translated by the FHR monitor as an equipment malfunction error. Such error conditions can be displayed to alert the operator. In the alternative, the improved LVDS receiver chip 406 outputs a square pulse, logic high and low change with the same frequency as the input signal when the correct operation is detected (cable conductors are physically and electrically intact between the fetal monitor and the LVDS receives both inputs IN+ and IN−). The improved LVDS receiver chip 406 output can be latchable such that when an error condition is detected even if intermittently once, the improved LVDS receiver chip 406 output is latched logic high until the system is reset. This prevents temporary error conditions from allowing the operator to believe the cable is operating correctly.

In an exemplary embodiment, the LVDS receiver chip 406 functioning in accordance with state table 404 can be a single semiconductor 406 or a combination of more than one semiconductor that accomplishes the desired operations, as may be required and/or desired in a particular embodiment.

Resetting of the error condition can be done by way of cycling power on the fetal monitor, replacing the cable 330 which also cycles power on the transducer, or other suitable resetting methods, as may be required and/or desired in a particular embodiment.

In operation, the failsafe LVDS 406 circuit not only detects intermittent or broken wire (from cable 330) conditions but also detects both inputs LVDS +/− (twisted pair conductors) open or short-circuited. The present invention, improved LVDS receiver IC semiconductor 406 with input failure detection logic circuit as shown in reference 'A' and 'C'. The output of the LVDS 406 is then received by the microcontroller (MCU) or CPLD 408 by way of, as needed, additional latching, tri-state buffering, other types of buffering, or other signal processing circuitry 410.

In an exemplary embodiment, such improved LVDS semiconductor 406 can be fabricated in a form factor and pin-compatible manner so that the improved failsafe LVDS 406 can be a direct semiconductor part replacement in prior transducers that suffer from the shortcomings mentioned above. Alternatively, separate failsafe circuitry 400 can be incorporated into existing frontend PCB 114 or backend PCB 126 to detect cable failed conditions, as may be required and/or desired in a particular embodiment.

In an exemplary embodiment and with reference to reference 'C', an electronic control system 400 comprises a low voltage differential signal (LVDS) receiver having an IN+ input (cable 330 pin 3), an IN− input (cable 330 pin 2), and an output 412. The LVDS receiver 406 monitors the operational status of the fetal heart rate transducer 100/200 by generating at output 412 a first logic state corresponding to a logic level high (H) or a second logic state corresponding to a logic level low (L) as follows:

when the difference between the IN+ 424 and the IN− 422 is greater than or equal to 100 mv the output 412 is the first logic state (such as logic high (H));

when the difference between the IN+ 424 and the IN− 422 is less than or equal to 100 mv the output 412 is the second logic state (such as a logic low (L));

when the IN+ 424 is open (not connected) the output 412 is the first logic state (such as logic high (H));

when the IN− 422 is open (not connected) the output 412 is the first logic state (such as logic high (H));

when the IN+ 424 and IN− are connected by a first resistance 414, which is configured as an undriven parallel termination, the output 412 is the first logic state (such as logic high (H));

when IN+ 424 is shorted to the supply voltage (Vcc) 426 or ground 428 the output 412 is the first logic state (such as logic high (H));

when IN− is shorted to Vcc 426 or ground 428 the output 412 is the first logic state (such as logic high (H)); and when IN+ 424 and IN− 422 are shorted together the output 412 is the first logic state (such as logic high (H)).

In operation, the first logic state is either logic level high (H) or logic level low (L) and the second logic state is the opposite of the first logic state. For disclosure purposes and not as a limitation, as illustrated in FIG. 22 and described above the first logic state has been selected as logic level high (H) and the second logic state has been selected as a logic level low (L).

Additionally, the first logic state is latched on output 412, requiring a reset to clear latching of output 412, when the first logic state persists on output 412 for more than a predetermined error condition time period. In this regard, while normal operation 418 sees the difference between IN+ 424 and IN− 422 transitioning 416 between greater than or equal to 100 mv and less than or equal to 100 mv causing output 412 to transition 416 between the first logic state and the second logic state if the output 412 remains at the first logic state for an extended period of time (exceeding the predetermined error condition time period) something is wrong as illustrated in the state table 420 and the output 412 is latched to the first logic state which stops FHR detection until the transducer 100 is reset. A reset can be done by unplugging the transducer 100 from the fetal monitor 302 (removing power temporarily), changing cables, or other suitable reset methods. The predetermined error condition time period can be set in the range of milliseconds to seconds, as may be required and/or desired in a particular embodiment.

An advantage, in the present invention, is that by latching the output 412 when an error condition in the state table 420 is detected, displaying an incorrect FHR is prevented. As one example, the error condition when one of IN+ 424 or IN− 422 is open (not connected) an erroneous waveform can be created that is interpreted by the fetal monitor 302 as an FHR in the range of 220 beats per minute even when the transducer 100 is not connected to a patient 502. The present invention solves this error condition and others by latching output 412 to the first logic state when output 412 has been at the first logic state for a time period that exceeds the predetermined error condition time period preventing incorrect FHR readings from being displayed on the fetal monitor 302 and requiring a technician to remove from service broken cables 330 and/or transducer 100.

Figure 23:
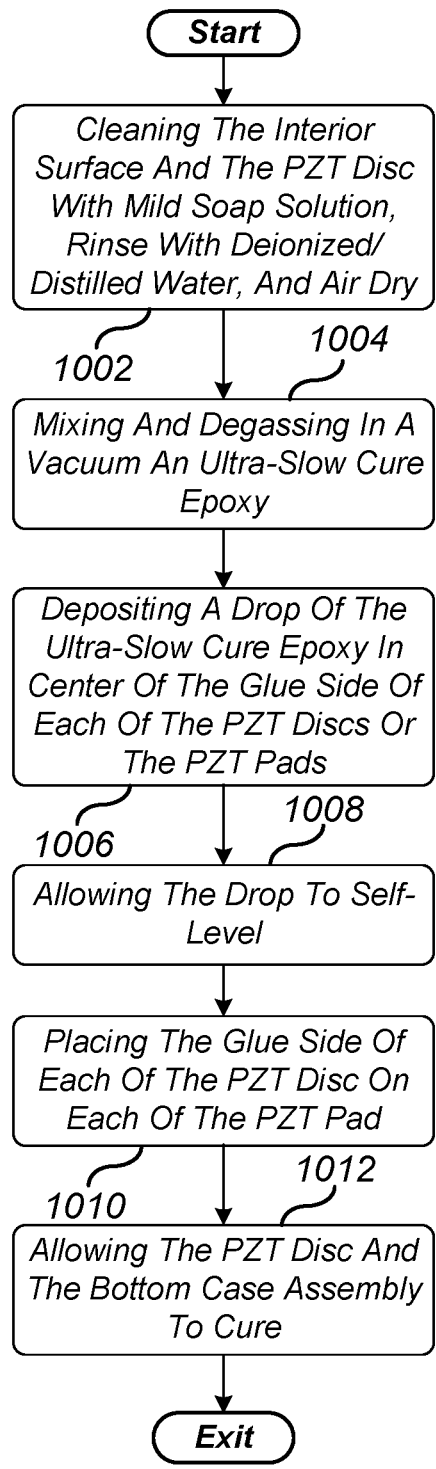
FIG. 23 illustrates one example of a method of adhering PZT discs to PZT pads.

Referring to FIG. 23, there is illustrated one example of a method of adhering PZT discs 112/218 to PZT pads 138/232. In an exemplary embodiment, the method begins in step 1002.

In step 1002, the interior surface 156/234 of the bottom case 106/204 and surfaces of the PZT discs 112/218 are cleaned with a mild soap solution, rinsed with deionized/distilled water, and air dried.

In an exemplary embodiment, if the transducer is being reworked, then patches of old epoxy should be removed. Such patches of old epoxy can often be removed by placing them is a multi-frequency ultrasound cleaner until clean. The PZT disc 112/218 and frontend PCB 114 should not be scraped as scratches will not allow uniform bonding film of epoxy and the ultrasound beam profile will deteriorate due to increased diffraction of the wavefront from the scratched area that would result in the ultrasound beam quality parameters to be non-compliant with OEM specifications approved by FDA.

In most cases, it is relatively easy to remove old epoxy from the plastic surface as there are often air pockets. One method is to soak the area with distilled warm water for 15 to 20 minutes and carefully peel off the old glue using forceps with the aid of looking through a 10× magnifier lens or a microscope. In all cases regardless of the method of glue removal used, utmost care should be taken so that the plastic surface is not scratched. The second method of old glue removal can include using isopropyl alcohol or white vinegar. Once the old glue is completely removed, the step of cleaning can proceed.

Once cleaned, the PZT discs 112/218, frontend PCB 114, and plastic substrate of the bottom case 106/204 can be inspected under a 10× magnifier lens/microscope to ensure there are no scratches or dust particles. Care should be taken to avoid touching any bonding surfaces after cleaning is finished to avoid introducing oils or contaminants on the bonding surfaces.

In an exemplary embodiment, the cleaned plastic bottom case 106/204, the PZT discs 112/218, and frontend PCB 114 (surface to be epoxied facing upward) should be placed on a work table that is perfectly horizontally level and has a top surface with mirror finish RA 0.1 μm (micrometer). Care should also be observed by wearing static protection wristband to handle the frontend PCB 114 as CMOS integrated circuits, and other components are susceptible to electrostatic discharge damage. The method moves to step 1004.

In step 1004, an ultra slow-cure epoxy 162 is mixed and degassed in a vacuum, for a first degas time period.

In an exemplary embodiment, the ultra slow-cure epoxy 162 is mixed in four-parts resin, one-part hardener ratio (4:1) by volume in a pot. The pot is then placed in a vacuum chamber to degas for 15 to 20 minutes at 26 in Hg. Once degassed, a 5 ml control sample of the ultra slow-cure epoxy 162 is placed on a 0.1 mm thick polyethylene paper and set aside as a batch quality control sample. The method then moves to step 1006.

In step 1006, a drop of the ultra slow-cure epoxy 162 is deposited in the center of the epoxy side 160/246 of each of the PZT discs 112/218 while the PZT disc 112/218 is resting on a horizontal surface with the epoxy side 160/246 up, or the PZT pad 138/232 while the bottom case 106/204 is resting on a horizontal surface.

In an exemplary embodiment, a 3 ml DYMAX syringe or similar is filled with degassed ultra slow-cure epoxy 162 and placed in a stepper dispenser such as a DYMAX STEPPER, or other suitable stepper dispensers that is configured for 0.2 ml epoxy drops for 10 mm diameter PZT discs and 0.24 ml for 11.9 mm diameter PZT discs. At the start of epoxy dispensing the first epoxy shot is discarded to prepare the stepper dispenser. Each successive epoxy shot is dispensed at the center of each horizontally laid PZT disc. One filling of a 3 ml syringe should deliver approximately 14 shots (plus the first shot unused) to cover 14 PZT discs. In the alternative, the stepper dispenser can place the epoxy drops on the PZT pads instead of the PZT discs and the method continued. The method then moves to step 1008.

In step 1008, the drop of ultra slow-cure epoxy 162 is allowed to self-level for a self-leveling time period. In an exemplary embodiment, the ultra slow-cure epoxy 162 drops are allowed to self-level for 15 to 20 minutes on the PZT disc surface 112/218. In the alternative, when the ultra slow-cure epoxy 162 drops can be placed on the PZT pads 138/232 instead of the PZT discs 112/218, the bottom case 106/204 can be maintained on a level surface for the self-leveling time period and the method continued. The method then moves to step 1010.

In step 1010, the epoxy side 160/246 of each of the PZT discs 112/218 is placed on each of the PZT pads 138/232 while the bottom case 106/204 is resting on a horizontal surface.

In an exemplary embodiment, the PZT discs 112/218 are picked up by holding the edges diagonally and placed on the PZT pads 138/232. In an exemplary embodiment, when the frontend PCB 114 has previously been bonded to the interior surface 156 of the bottom case 106, the PZT discs 112/218 can be placed through the PZT holes 116 in the frontend PCB 114 in the center, and a one-part silicone dots can be placed on the diagonally opposite positions of the PZT disc 112 and frontend PCB 114 proximate the edge of the PZT hole 116 to hold the PZT disc 112 in the center of the PZT hole 116. The method then moves to step 1012.

In step 1012, the PZT disc 112/218 and the bottom case 106/204 assembly are allowed to cure for a cure time period. In an exemplary embodiment, the PZT disc 112/218 self-levels under its own weight during the cure time period. Such a cure time period can be a minimum of 68 hours and/or until the control sample develops a film formed on the polyethylene sheet that does not get pierced with a Shore A hardness durometer needle. The method is then exited.

Figure 24:
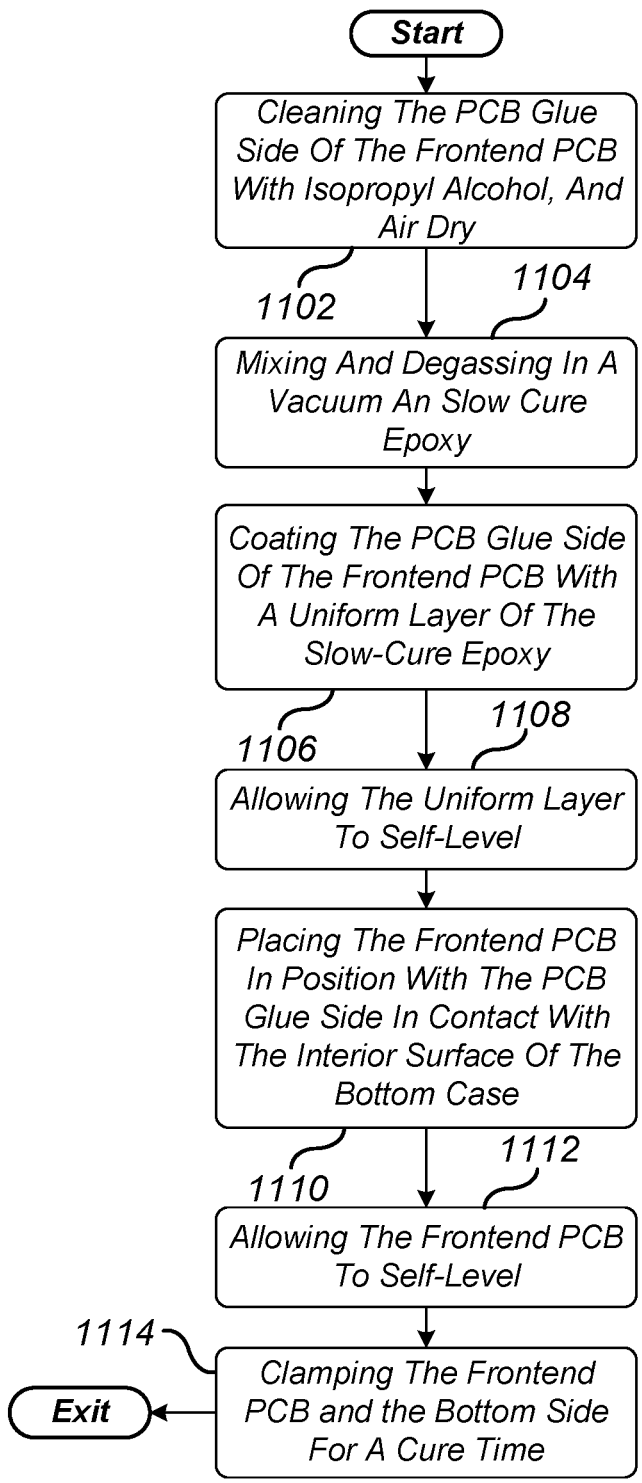
FIG. 24 illustrates one example of a method of adhering the frontend PCB to the interior surface of the bottom case.

Referring to FIG. 24, there is illustrated one example of a method of adhering the frontend PCB 114 to the interior surface 156 of the bottom case. In an exemplary embodiment, the method begins in step 1102.

In step 1102, the PCB epoxy side 166 of the frontend PCB 114 is cleaned with isopropyl alcohol, and air dry. The method then moves to step 1104.

In step 1104, a slow-cure epoxy 168 is mixed and degassed in a vacuum, for a degas time period.

In an exemplary embodiment, a slow-cure epoxy 168 is mixed by volume in a pot with two parts resin to one part hardener (2:1). The slow-cure epoxy 168 is then degassed by placing the pot in a vacuum chamber to a degas time period of 8 to 10 minutes at 26 inches of Hg. The method then moves to step 1106.

In step 1106, the PCB epoxy side 166 of the frontend PCB 114 is coated with a uniform layer of the slow-cure epoxy 168 while the frontend PCB is resting on a horizontal surface with the PCB epoxy side 166 up.

In an exemplary embodiment, a Teflon rod can be used to apply degassed slow-cure epoxy 168 to the PCB epoxy side 166 of the frontend PCB forming a uniform thin layer of the slow-cure epoxy 168. The method then moves to step 1108.

In step 1108, the uniform layer of the slow-cure epoxy 168 is allowed to self-level for a self-leveling time period. In an exemplary embodiment, the self-leveling time period can be 10 to 15 minutes. The method then moves to step 1110.

In step 1110, the frontend PCB 114 is placed in position with the PCB epoxy side 166 in contact with the interior surface 156 of the bottom case 102. In an exemplary embodiment, excess slow-cure epoxy 168 around the edges of the frontend PCB 114 can be wiped away prior to placing the frontend PCB 114 in the proper orientation on the interior surface of the bottom case 102. The method then moves to step 1112.

In step 1112, the frontend PCB 114 is allowed to self-level for a self-leveling time period. In this regard, the self-leveling time period can be 10 to 15 minutes allowing the frontend PCB 114 to self-level on its own weight. The method then moves to step 1114.

In step 1114, the frontend PCB 114 and the bottom case 102 can be clamped at more than one pressure point 822/824 for a cure time. The pressure points 822 are symmetrically located on the surface of the top side 164 of the frontend PCB 114.

In an exemplary embodiment, excess slow-cure epoxy 168 can be wiped from the edges of the frontend PCB 114 and/or interior surface 156 of the bottom case 102. The frontend PCB 114 and the bottom case 102 can then be clamped together in at least four spots 822 symmetrically placed on the frontend PCB 114. The slow-cure epoxy 168 cure time can be in the range of 24 to 36 hours depending on the room temperature.

In an exemplary embodiment, the slow-cure epoxy 168 bonding method can also be used for the over-molding polyurethane/elastomer cover on the top case 106 and bottom 106 cases to enhance the durability of the transducer 100.

Figure 25:
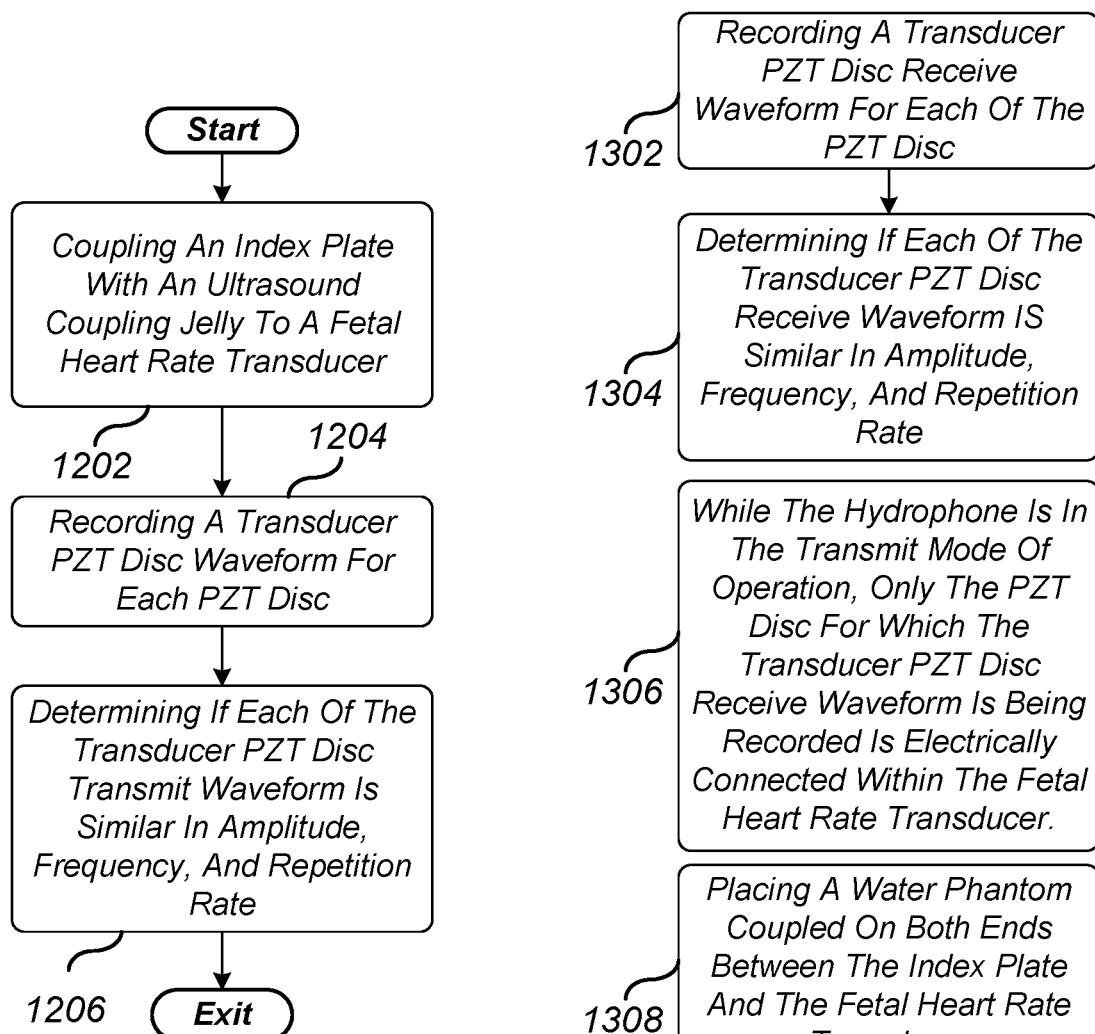
FIG. 25 illustrates one example of a method of using an improved fetal heart rate transducer.

Referring to FIG. 25, there is illustrated one example of a method of using an improved fetal heart rate transducer 100/200. In an exemplary embodiment, one method of using the improved fetal heart rate transducer 100/200 is in combination with a hydrophone 600 which is better illustrated in at least FIGS. 27 and 28. In this regard, reworked as well as new transducers can be checked to ensure that the PZT discs 112/218 and frontend PCB 114 are properly bonded to the bottom case 106/204. The method begins in step 1202.

In step 1202, an index plate 702 is coupled with an ultrasound coupling jelly 712 to an improved fetal heart rate transducer 100/200. In an exemplary embodiment, the index plate 712 has more than one PZT disc position hole 704 that corresponds to and correlates with the location of each of the more than one PZT disc 112/218 within the fetal heart rate transducer 100/200. The fetal heart rate transducer 100/200 comprises a top case and a bottom case that fastens to the top case. The bottom case comprises an interior surface. The interior surface 156/234 has de-embossed or raised more than one PZT pad 138/232, and more than one standoff 110/228/230. More than one metal insert 108/222/224 is molded into place within the standoff as the bottom case is fabricated. More than one PZT disc 112/218 has a top side 158/244 and an epoxy side 160/246.

Each of the PZT discs 112/218 adheres to the PZT pad 138/232 as follows, cleaning the interior surface 156/234 and the PZT disc 112/218 with mild soap solution, rinsing with deionized/distilled water, and air drying. Mixing and degassing in a vacuum, for a first degas time period, an ultra slow-cure epoxy 162.

Depositing a drop of the ultra slow-cure epoxy 162 in the center of the epoxy side 160/246 of each of the PZT discs 112/218 while the PZT disc 112/218 is resting on a horizontal surface with the epoxy side 160/246 up, or the PZT pad 138/232 while the bottom case 106/204 is resting on a horizontal surface. Allowing the drop of ultra slow-cure epoxy 162 to self-level for a first self-leveling time period. Placing the epoxy side 160/246 of each of the PZT discs 112/218 on each of the PZT pads 138/232 while the bottom case 106/204 is resting on a horizontal surface. And, allowing the PZT disc 112/218 and the bottom case 106/204 assembly to cure for a first cure time period. The method then moves to step 1204.

In step 1204, a transducer PZT disc transmit waveform 808 is recorded for each of the PZT discs 112/218, by way of an oscilloscope 812 that is operationally connected to a hydrophone 600 that is in a receive mode (602/614 connected together by switch 612), by placing a hydrophone PZT disc 604 that is bonded to plastic substrate 606 and operationally related to the hydrophone 600 into one of the PZT disc position hole 704 and recording one of the transducer PZT disc transmit waveform 808 corresponding to one of the PZT disc 112/218, and repeating by moving the hydrophone PZT disc 604 to a different one of the PZT disc position hole 704 until at least one of the transducer PZT disc transmit waveform 808 has been recorded at each of the PZT disc position hole 704. The method then moves to step 1206.

In step 1206, a determination is made as to whether each of the transducer PZT disc transmit waveform 808 is similar in amplitude 806, frequency 808, and repetition rate 810 indicating that the fetal heart rate transducer 100/200 is transmitting properly and that each of the PZT disc 112/218 is uniformly bonded to the interior surface of the bottom case of the fetal heart rate transducer 100/200.

In an exemplary embodiment, transducers 100/200 that are new, reworked, and/or post being drop tested on a concrete floor can be checked with this method to see if any of the PZT discs 112/218 have dislodged partially or completely.

Figure 26:
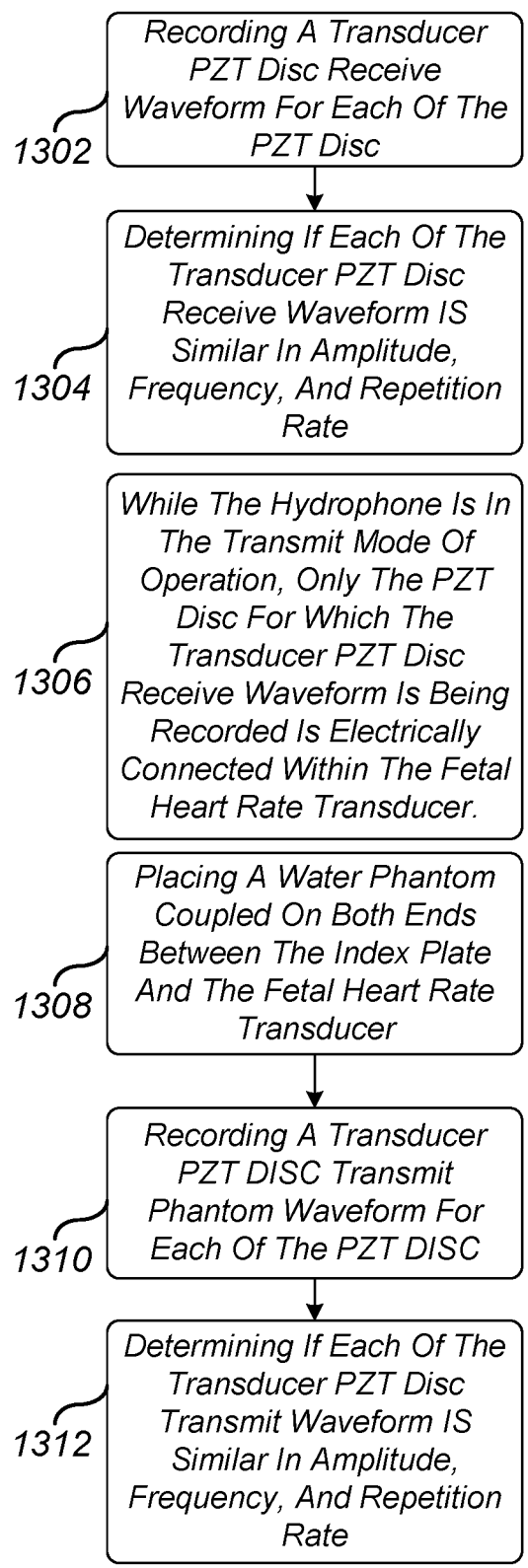
FIG. 26 illustrates exemplary embodiments that can be used interchangeably with the methods of the present invention.

Referring to FIG. 26, there are illustrated exemplary embodiments that can be used interchangeably with the methods of the present invention.

In step 1302, a transducer PZT disc receive waveform 808 is recorded for each of the PZT discs 112, by way of the oscilloscope 812. The oscilloscope 812 is operationally connected to the output of a pre-amp 622 of the fetal heartbeat transducer 100 while the hydrophone 600 is in a transmit mode (602/610 connected by way of switch 612). By placing the hydrophone PZT disc 604 bonded to substrate 606 into one of the PZT disc position hole 704 and recording one of the transducer PZT disc receive waveform 808 corresponding to one of the PZT disc 112, and repeating by moving the hydrophone PZT disc 604/606 to a different one of the PZT disc position hole 704 until at least one of the transducer PZT disc receive waveform 808 has been recorded for each of the PZT disc position hole 704. The method then moves to step 1304.

In step 1304, a determination is made if each of the transducer PZT discs receives waveform 808 is similar in amplitude 806, frequency 808, and repetition rate 810 indicating the fetal heart rate transducer 100 is receiving properly, and that each of the PZT disc 112 is uniformly bonded to the case of the fetal heart rate transducer 100.

In step 1306, while the hydrophone 600 is in the transmit mode (602/610 connected by way of switch 612) of operation, only the PZT disc 112 for which the transducer PZT disc receives waveform 808 is being recorded, is electrically connected within the fetal heart rate transducer 100. The other PZT discs 112 are electrically disconnected.

In step 1308, a water phantom 706/708/710 is placed and coupled on both ends with the ultrasound coupling jelly 712 between the index plate 702 and the fetal heart rate transducer 100. The method then moves to step 1310.

In step 1310, a transducer PZT disc transmits phantom waveform 808 is recorded for each of the PZT discs 112, by way of the oscilloscope 812. The oscilloscope 812 is operationally connected to the hydrophone 600 that is in the receive mode (602/614 connected by way of switch 612), by placing a hydrophone PZT disc 604/606 that is operationally related to the hydrophone 600 into one of the PZT disc position hole 704 and recording one of the transducer PZT disc transmits phantom waveform 808 corresponding to one of the PZT disc 112 and repeating by moving the hydrophone PZT disc 604/606 to a different one of the PZT disc position hole 704 until at least one of the transducer PZT disc transmits phantom waveform 808 has been recorded at each of the PZT disc position hole 704. The method then moves to step 1312.

In step 1312 a determination is made if each of the transducer PZT discs transmit phantom waveform 808 is similar in amplitude 806, frequency 808, and repetition rate 810 through the first water phantom (one of 706/708/710) indicating uniform field strength and ultrasound beam field quality at height of the water phantom.

In an exemplary embodiment, the method of steps 1308, 1310, and 1312 can be repeated with different water phantoms 706, 708, or 710 having different heights 826, 816, and 818 respectively.

For disclosure purposes, the water phantoms 706, 708, and 710 are water-filled cylinders of a diameter 806 that is comparable to the diameter of the PZT discs 112 patterns when bonded to the bottom case 106. The heights 826, 816, and 818 of the water phantoms 706, 708, and 710 vary. In operation, passing ultrasound waves through a water phantom simulates passing ultrasound waves through the human body. In this regard, water phantoms allow methods that simulate the transducer 100 being used on patient 502 so that correct PZT disc 112/218 bonding and transducer operation can be quantitatively established through the use of a hydrophone 600, oscilloscope 812, and transducer 100/200.

Figure 27:
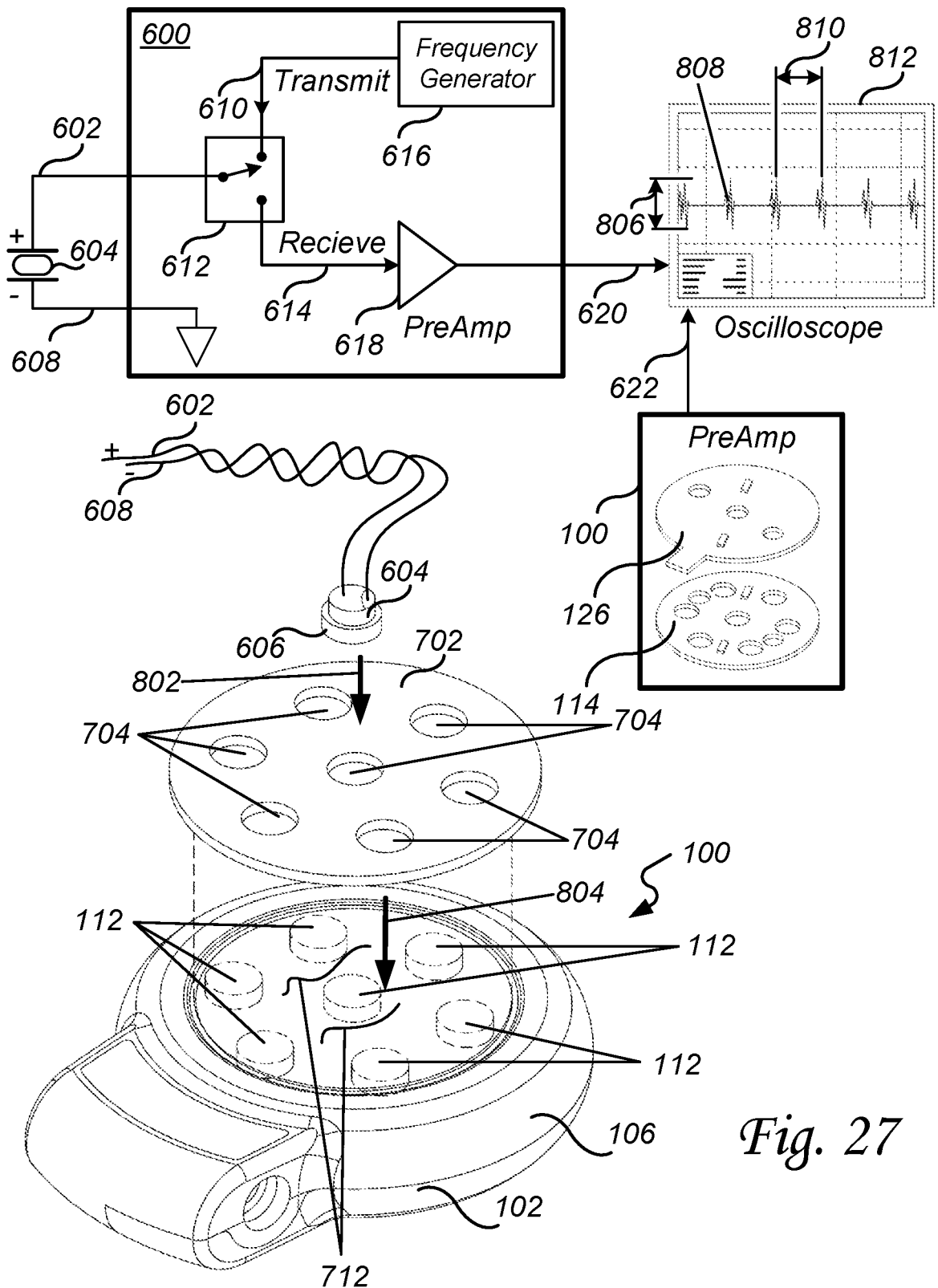
FIG. 27 illustrates one example of a hydrophone.

Referring to FIG. 27, there is illustrated one example of a hydrophone 600. In an exemplary embodiment, an index plate 702 can be fabricated from a 1 mm thick circular acrylic plate of 52.5 mm diameter, or other suitable size diameters with 7 holes of 12.4 mm to mimic the PZT disc 112 patterns of the transducer 100, forming PZT disc position hole 704. A PZT disc 604 can be bonded with the methods of the present invention to a plastic substrate 606 forming the hydrophone PZT disc 604/606. Electrically 602/608 wire leads can be connected to the hydrophone 600. The index plate 702 is coupled 804 to the bottom case 106 by way of ultrasound jelly 712 additionally the plastic substrate 606 when placed into one of the PZT disc position holes 704 is coupled with ultrasound jelly 712.

The hydrophone 600 comprises a frequency generator 616 that is matched to the transducer 100 center frequency of 1 MHZ+/−100 Hz and the pre-amp 618 is also identical to the pre-amp 622 from the transducer 100. The PZT disc 604 used in the hydrophone is also an exact match to the PZT disc 218 from the transducer 100. A toggle switch 612 enables the hydrophone 600 to be placed in a transmit mode of operation where 602 and 610 are connected together by way of switch 612 or a receive mode of operation where 602 and 614 are connected together by way of switch 612.

In the transmit mode of operation, the frequency generator 616 couples the generated frequency to the hydrophone PZT disc 604/606 which broadcast an ultrasound wave that can be detected by the PZT 112 disc with the target transducer 100. The ultrasound wave is received by one or more of the PZT disc 112. The PZT disc 112 is coupled to the frontend PCB 114 which is interconnected with the backend PCB 126. A preamp associated with the PCB 114/126 processes the ultrasound wave from the PZT disc 112 and the preamp output 622 is coupled to the oscilloscope 812 where the transducer PZT disc receives waveform 808 can be observed and recorded.

In a method of using the hydrophone 600, the top case 102 of the transducer 100 can be removed and a 6 to 8-inch long twisted pair cable can be connected to the output of the pre-amplifier 622 on the frontend PCB 114 or backend PCB 126 depending on where the pre-amplifier is located. The other end of the twisted pair cable 622 can be connected to the oscilloscope 812.

All but one of the PZT discs 112 can be disconnected by desoldering +V 194/294 electrode connection on the PZT disc 112 (−V 196/296 can stay connected). Additionally, the oscillator output can be disabled to turn off the transmission mode. The dismantled transducer 100 can be placed face-up on a leveled fixture. The index plate 702 can be coupled with ultrasound coupling jelly 712 to the face of the transducer 100 with the PZT disc position hole 704 aligned with the PZT disc 112. The hydrophone PZT disc 604/606 can be placed in the PZT disc position hole 704 corresponds to the PZT disc that is electrically connected, the plastic substrate 606 is coupled to the surface of the transducer 100 within the selected PZT disc position hole 704 with ultrasound coupling jelly 712.

The switch 612 is positioned in the transmit mode of operation, where 602/610 are connected together by way of the switch 612 and the transducer 100 is connected to power on the fetal monitor 302. The transducer PZT disc receive waveform 808 can then be displayed and recorded on the oscilloscope 812.

The method can be continued by electrically connecting one of the PZT discs 112, one at a time, moving the hydrophone PZT disc 604/606 to the corresponding PZT disc position hole 704, and recording the transducer PZT disc receive waveform 808 for each PZT disc 112 until all readings are complete.

All the readings can then be compared for identical amplitude 806, frequency 808, and repetition rate 810 to confirm the correct bonding of the PZT disc to the interior surface of the bottom case 106, as well as the transducer 100 correct receiving.

In the receive mode of operation, the hydrophone PZT disc 604/606 receives ultrasound waves generated by the PZT disc 112. The received ultrasound wave is coupled to a preamp 618 and the preamp 618 is coupled 620 to an oscilloscope 812.

In a method of using the hydrophone 600, a transducer 100 can be placed on a table with a proper fixture so that its face is up and perfectly leveled horizontally. The indexing plate 702 is coupled with ultrasound coupling jelly 712 to the face of transducer 100. The transducer 100 is connected to the fetal monitor and power is applied. Ultrasound coupling jelly 712 is applied to the plastic surface 606 of hydrophone 600 and placed in one of the PZT disc position holes 704. The toggle switch 612 is set to the receive mode and the pre-amp 618 output 620 transducer PZT disc transmit mode waveform 808 is displayed and recorded on the oscilloscope 812.

Transducer PZT disc transmit waveform 808 measurements can be made for all other positions of PZT discs 112 in the index plate 704 by placing the hydrophone PZT disc 604/606 in a different one of the respective indexing plate hole 704 and recording then verifying that all the seven waveform readings are identical having the same amplitude 806, frequency 808, and repetition rate 810.

Referring to FIG. 28, there is illustrated one example of a hydrophone used in combination with a plurality of water phantoms. In an exemplary embodiment, a quantitative test can be used to assess ultrasound beam quality, transmission, and reception characteristics of the PZT disc 112/218 as well as the bond integrity of the PZT disc and frontend PCB 114.

For disclosure purposes, the water phantoms 706, 708, and 710 are water-filled cylinders of a diameter 806 that is comparable to the diameter of the PZT discs 112 patterns when bonded to the bottom case 106. The heights 826, 816, and 818 of the water phantoms 706, 708, and 710 vary. In operation, passing ultrasound waves through a water phantom simulates passing ultrasound waves through the human body. In this regard, water phantoms allow methods that simulate the transducer 100 being used on patient 502 so that correct PZT disc bonding and transducer operation can be quantitatively established through the use of a hydrophone 600, oscilloscope 812, and transducer 100.

In operation, a cylindrical water phantom 706 of 52.5 mm diameter 806, and 35 mm in height 826 can be coupled with ultrasound coupling jelly on one end with the index plate 702 and the other end to the front surface of the transducer 100. The PZT disc position hole 704 is aligned with the PZT disc 112. The hydrophone PZT disc 604/606 is placed into one of the PZT disc position holes 704 and coupled with ultrasound coupling jelly 712 to the phantom 706.

The hydrophone 600 is placed in the receive mode of operation and the transducer PZT disc transmits through phantom waveform 808 corresponding to one of the PZT disc 112 is displayed on the oscilloscope 812 and recorded. The method can be repeated for each PZT disc 112 by moving the hydrophone PZT disc 604/606 to a different one of the PZT disc position hole 704 until at least one of the transducer PZT disc receives phantom waveform 808 has been recorded at each of the PZT disc position hole 704. A determination can then be made if each of the transducer PZT discs receives phantom waveform 808 is similar in amplitude 806, frequency 808, and repetition rate 810 indicating uniform field strength and ultrasound beam field quality at the height of the water phantom.

In an exemplary embodiment, in operation, only one of the transducer PZT disc 112 is connected for transmission at a time and the other PZT disc 112 is an open circuit by removing one of the wire leads when one of the water phantoms is used. When water phantom is not used, meaning the hydrophone PZT disc 604/606 is directly coupled onto the bottom case 102 plastic substrate to measure transmission from one of the PZT disc 112 then all other transducer PZT discs can be connected and continue transmitting as such transmissions do not interfere with results.

Measurements can be repeated for the phantoms with 85 mm height 816 and 150 mm height 818 to confirm the waveform measurements are identical on every transverse plane of the ultrasound beam path.

The functional performance of the transducer units 100/200 after bonding the PZT discs 112/218, 7 PZT discs 112, or 9PZT discs 218 can be carried out the same way.

Figure 29:
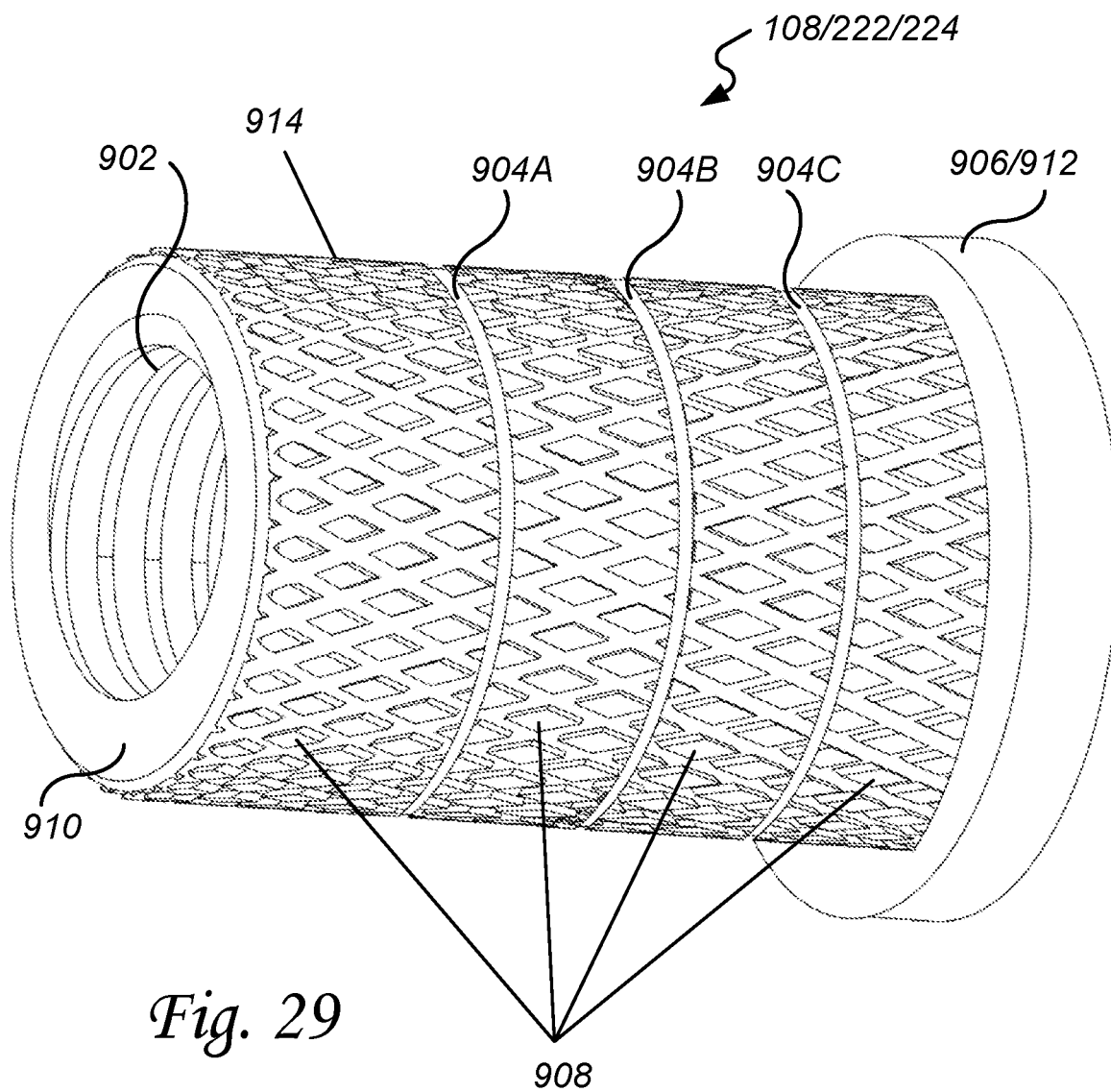
FIG. 29 illustrates one example of an insert.

Referring to FIG. 29, there is illustrated one example of a metal insert 108/222/224. In an exemplary embodiment, the metal insert 108/222/224 is cylindrical having an insert top end 910, an insert bottom end 912, and a cylindrical body 914. A diamond-shaped knurling 908 is present around the circumference of the body 914. A raised ridge 906 extends around the circumference of body 914 at the bottom end 912, and more than one groove 904A-C is spaced along and extends around the circumference of body 914. The metal insert 108/222/224 is molded into the standoff 110/228/230 with the bottom end 912 closest to the inside of the interior surface 156/234 plastic substrate and the top end 910 co-planar with the top of the standoff 110/228/230 in a manner to receive and fasten with the machine screw 134/210/214.

In an exemplary embodiment, the metal insert 108/222/224 can be made of brass, steel, or other suitable metals, as may be required and/or desired in a particular embodiment.

Referring to FIG. 30, there is illustrated one example of Doppler equations for frequency shift calculation.

Referring to FIG. 31, there is illustrated one example of a cable 330 assembly. An advantage, in the present invention, is that, unlike prior cables that connect transducers 100 to fetal monitors 302 and notoriously fail where crimped and over-molded, the present invention, utilizes a fetal monitor end connector 348A/348B that has a hollow rigid body 340 made of plastic and a connector top 336 that can be fastened by way of the screw hole 346 and standoff 362 to the hollow rigid body 340. Additionally, a strain relief 344 made out of 60A shore hardness elastomer can be fitted into an integrally formed groove end 360 to secure cable 350 from pulling out of the hollow ridge body 340.

For disclosure purposes, fetal monitor end connectors 348A/348B are two different styles that interface to different models of fetal monitor 302. Other shaped types and kinds of fetal monitor end connectors 348 can be utilized as may be required and/or desired in a particular embodiment.

In an exemplary embodiment, the hollow rigid body 340 can be filled with silicon. In an alternative approach, the connector top 336 and standoff 362 can be eliminated and the hollow rigid body 340 can be filled and or otherwise sealed with silicon.

Additionally, the use of secondary strain relief 342 inside the hollow rigid body 340 further protects the cable 350 against pulling forces and relieves stress on the individual conductors 338 that are crimped/soldered on contact pins located at the wire connection end 362. In an exemplary embodiment, such secondary strain relief 342 can be at least two tie wraps or other suitable strain relief.

In an exemplary embodiment, electronic-grade silicone can be filled inside to make the connector compliant with IP68 specifications for water ingress. The increased length of the hollow rigid body 340 compared to the length of prior rubber over-molded approaches makes it easier for an operator to grab the hard-plastic connector for connecting and disconnecting from the fetal monitor 302.

In an exemplary embodiment, the transducer connector 352 terminates the individual conductors 338 on the opposite end of cable 350. The transducer connector 352 connects to the frontend PCB 114 or the backend PCB 126. Strain relief 354 and rubber boot 358 secure the cable 350 by way of the cable connector 104/140 entry hole/cavity inside the transducer 100.

In an exemplary embodiment, the improved fetal heart rate transducer 100 can comprise a cable 350 having a first cable end 350A and a second cable end 350B. A fetal monitor connector 348A/348B comprises a hollow rigid body 340 having a wire connection end 362 and an integrally formed grooved end 360. A strain relief 344 is placed over the first cable end 350A and secured within the integrally formed grooved end 360 holding the first cable end 350A from slipping out of the hollow rigid body 340.

In an exemplary embodiment, a secondary strain relief 342 can be fastened around the first cable end 350A within the hollow rigid body 340 proximate to the strain relief 360.

In an exemplary embodiment, such secondary strain relief 342 can be at least two tie wraps fastened in parallel around the first cable end 350A within the hollow rigid body 340 proximate to the strain relief 360.

The secondary strain relief 342 further prevents the first cable end 350A from being pulled out of the hollow rigid body 340. More than one conductor 338 from the first cable end 350A terminates with electrical connections at the wire connection end 362. The fetal monitor connector 348A/348B plugs into a fetal monitor 302, and the second cable end 350B terminates with a transducer connector 352.

In an exemplary embodiment, an improved fetal heart rate transducer 100/200 comprises a top case 106/210A/210B, and a bottom case 106/204 that fastens to the top case 106/210A/210B, the bottom case 106/204 comprises an interior surface, the interior surface comprises de-embossed or raised more than one piezo-electric crystal (PZT) pad 138/232.

More than one PZT disc 112/218, each PZT disc 112/218 adheres to the PZT pad 138/232, a frontend printed circuit board (PCB) 114/216 is secured to the bottom case 106/204 and is operationally related to the PZT disc 112/218. A cable 330 has a first cable end 350A and a second cable end 350B. A fetal monitor connector 348A/348B comprises a hollow rigid body 340 having a wire connection end 362 and an integrally formed grooved end 360. A strain relief 344 is placed over the first cable end 350 and secured within the integrally formed grooved end 360 holding the first cable end 350A from slipping out of the hollow rigid body 340.

And, a secondary strain relief 342 is fastened around the first cable end 350A within the hollow rigid body 340 proximate to the strain relief 340. Wherein the secondary strain relief 342 further prevents the first cable end 350A from being pulled out of the hollow rigid body 340. More than one conductor 338 from the first cable end 350A terminates with electrical connections 338 at the wire connection end 362. Wherein the fetal monitor connector 348A/348B plugs into a fetal monitor 302, and the second cable end 350B terminates with a transducer connector 352, the transducer connector 352 connects to the frontend PCB 114/216.

In an exemplary embodiment, the secondary strain relief 342 can be at least two tie wraps that are fastened in parallel around the first cable end 350A within the hollow rigid body 340 proximate to the strain relief 340.

In an exemplary embodiment, the hollow rigid body 340 can be filled with silicon, and a connector top 336 can be fastened by way of the screw hole 346 and standoff 362 to seal fetal monitor connector 348A/348B including the hollow rigid body 340.

In an alternative approach, the connector top 336 and standoff 362 can be eliminated, and fetal monitor connector 348A/348B including the hollow rigid body 340 can be filled and or otherwise sealed with silicon.

The capabilities of the present invention can be implemented in software, firmware, hardware, or some combination thereof.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. An improved fetal heart rate transducer comprising:
a top case;
an ultra slow-cure epoxy;
a bottom case fastens to the top case, the bottom case comprises an interior surface, the interior surface comprises more than one of a standoff, and de-embossed or raised more than one of a piezo-electric crystal (PZT) pad;
more than one of a metal insert is molded into place within the standoff as the bottom case is fabricated; and
more than one of a PZT disc having a top side and an epoxy side, each of the PZT disc adheres to the PZT pad as follows:
cleaning the interior surface and the PZT disc;
mixing and degassing in a vacuum, for a first degas time period, the ultra slow-cure epoxy;
depositing a drop of the ultra slow-cure epoxy in center of the epoxy side of each of the PZT disc while the PZT disc is resting on horizontal surface with the epoxy side up, or the PZT pad while the bottom case is resting on horizontal surface;
allowing the drop to self-level for a first self-leveling time period;
placing the epoxy side of each of the PZT disc on each of the PZT pad while the bottom case is resting on horizontal surface; and
allowing the PZT disc and the bottom case assembly to cure for a first cure time period.

2. The improved fetal heart rate transducer in accordance with claim 1, the first degas time period is 15 to 20 minutes, the first self-leveling time period is 15 to 20 minutes, the first cure time period is a minimum of 68 hours, the ultra slow-cure epoxy is mixed as four parts resin to one part hardener, and the size of the drop is in the range of 0.2 ml.

3. The improved fetal heart rate transducer in accordance with claim 1, the metal insert is cylindrical having an insert top end, an insert bottom end, and a cylindrical body, a diamond-shaped knurling is present around circumference of the cylindrical body, a raised ridge extends around circumference of the cylindrical body at the bottom end, and more than one of a groove is spaced along and extends around circumference of the cylindrical body, the metal insert is molded into the standoff with the bottom end closest to the interior surface and the top end co-planar with the top of the standoff in manner to receive and fasten with a machine screw.

4. The improved fetal heart rate transducer in accordance with claim 1, further comprising:
an electronic control system, the electronic control system comprises a low voltage differential signal (LVDS) receiver having an IN+ input, an IN− input, and an output, the LVDS receiver monitors operational status of the improved fetal heart rate transducer by generating at the output a first logic state or a second logic state as follows:
when difference between the IN+ and the IN− is greater than or equal to 100 mv the output is the first logic state;

when difference between the IN+ and the IN− is less than or equal to 100 mv the output is the second logic state;

when the IN+ is open (not connected) the output is the first logic state;

when the IN− is open (not connected) the output is the first logic state;

when the IN+ and IN− are connected by a first resistance, that is configured as an undriven parallel termination, the output is the first logic state;

when IN+ is shorted to Vcc or ground the output is the first logic state;

when IN− is shorted to Vcc or ground the output is the first logic state; and when IN+ and IN− are shorted together the output is the first logic state;

wherein the first logic state is either high or low and the second logic state is opposite of the first logic state;

wherein the first logic state is latched on the output, requiring a reset to clear latching of the output, when the first logic state persists on the output for more than a predetermined error condition time period.

5. The improved fetal heart rate transducer in accordance with claim 1, further comprising:

a slow-cure epoxy;

a frontend printed circuit board (PCB) having a PCB top side and a PCB epoxy side, each of the PZT disc interconnects with and are operationally related to the frontend PCB, the frontend PCB adheres to the interior surface of the bottom case as follows:

cleaning the PCB epoxy side of the frontend PCB;

mixing and degassing in a vacuum, for a second degas time period, the slow-cure epoxy;

coating the PCB epoxy side of the frontend PCB with a uniform layer of the slow-cure epoxy while the frontend PCB is resting on horizontal surface with the PCB epoxy side up;

allowing the uniform layer to self-level for a second self-leveling time period;

placing the frontend PCB in position with the PCB epoxy side in contact with the interior surface of the bottom case;

allowing the frontend PCB to self-level for a third self-leveling time period; and clamping, for a second cure time, the frontend PCB and the bottom case at more than one of a pressure point, the pressure point are symmetrically located on surface of the top side of the frontend PCB.

6. The improved fetal heart rate transducer in accordance with claim 5, the second degas time period is 8 to 10 minutes, the second self-leveling time period is 10 to 15 minutes, the third self-leveling time period is 10 to 15 minutes, the second cure time period is 24 to 36 hours, and the slow-cure epoxy is mixed as two parts resin to one part hardener.

7. The improved fetal heart rate transducer in accordance with claim 5, further comprising:

a backend PCB interconnects with the frontend PCB and is fastened at perimeter of the backend PCB to the bottom case by silicone.

8. The improved fetal heart rate transducer in accordance with claim 7, the bottom case comprises one or more of a raised island pad that extends from the interior surface of the bottom case to bottom surface of the backend PCB.

9. The improved fetal heart rate transducer in accordance with claim 1, further comprising:

a cable having a first cable end and a second cable end;

a fetal monitor connector comprises a hollow rigid body having a wire connection end and an integrally formed grooved end;

a strain relief is placed over the first cable end and secured within the integrally formed grooved end holding the first cable end from slipping out of the hollow rigid body; and at least two of a tie-wrap are fastened in parallel around the first cable end within the hollow rigid body proximate to the strain relief, wherein the tie wrap further prevents the first cable end from being pulled out of the hollow rigid body, more than one of a conductor from the first cable end terminates with electrical connections at the wire connection end;

wherein the fetal monitor connector plugs into a fetal monitor, and the second cable end terminates with a transducer connector, the transducer connector connects to the frontend PCB or the backend PCB.

10. The improved fetal heart rate transducer in accordance with claim 1, further comprising:

the top case comprises a top case top side, a top case interior surface, a top groove, a button fastener retainer, an inclined plane, more than one of a retaining clips, and more than one of a cupped standoff, the cupped standoff comprises a cupped standoff bottom that is integrally formed with the top case interior surface, and a cupped standoff top that has a raised ridge edge around circumference of the cupped standoff top creating a cavity that is sized to interconnect with the standoff on the bottom surface after passing through a frontend PCB and a backend PCB in a manner that allows the raised ridge edge to contact and immobilize the backend PCB from movement;

a threaded button fastener is inserted into the button fastener retainer from the top case interior surface side of the top case;

a threaded button is inserted through the top case top side into the threaded button fastener and tightened, securing the threaded button to the top case;

a cover covers the button fastener retainer and the threaded button fastener, the cover is secured under the retaining clips in a manner that the inclined plane applies force to the cover holding it from displacement from the retaining clips; and a gasket is fitted into the top groove and a bottom groove forming a seal between the top case and the bottom case when fastened together, the bottom case comprises the bottom groove.

11. An improved fetal heart rate transducer comprising:

a top case;

a bottom case that fastens to the top case, the bottom case comprises an interior surface, the interior surface comprises more than one of a standoff, and de-embossed or raised more than one of a piezo-electric crystal (PZT) pad;

more than one of a metal insert is molded into place within the standoff as the bottom case is fabricated;

more than one of a PZT disc having a top side and an epoxy side, each of the PZT disc adheres to the PZT pad; and an electronic control system, the electronic control system comprises a low voltage differential signal (LVDS) receiver having an IN+ input, an IN− input, and an output, the LVDS receiver monitors operational status of the improved fetal heart rate transducer by generating at the output a first logic state or a second logic state as follows:

when difference between the IN+ and the IN− is greater than or equal to 100 mv the output is the first logic state;
when difference between the IN+ and the IN− is less than or equal to 100 mv the output is the second logic state;
when the IN+ is open (not connected) the output is the first logic state;
when the IN− is open (not connected) the output is the first logic state;
when the IN+ and IN− are connected by a first resistance, that is configured as an undriven parallel termination, the output is the first logic state;
when IN+ is shorted to Vcc or ground the output is the first logic state;
when IN− is shorted to Vcc or ground the output is the first logic state; and
when IN+ and IN− are shorted together the output is the first logic state;
wherein the first logic state is either high or low and the second logic state is opposite of the first logic state;
wherein the first logic state is latched on the output, requiring a reset to clear latching of the output, when the first logic state persists on the output for more than a predetermined error condition time period.

12. The improved fetal heart rate transducer in accordance with claim 11, the metal insert is cylindrical having an insert top end, an insert bottom end, and a cylindrical body, a diamond-shaped knurling is present around circumference of the cylindrical body, a raised ridge extends around circumference of the cylindrical body at the bottom end, and more than one of a groove is spaced along and extends around circumference of the cylindrical body, the metal insert is molded into the standoff with the bottom end closest to the interior surface and the top end co-planar with the top of the standoff in manner to receive and fasten with a machine screw.

13. The improved fetal heart rate transducer in accordance with claim 11, further comprising:
an ultra slow-cure epoxy, each of the PZT disc adheres to the PZT pad as follows:
cleaning the interior surface and the PZT disc;
mixing and degassing in a vacuum, for a first degas time period, the ultra slow-cure epoxy;
depositing a drop of the ultra slow-cure epoxy in center of the epoxy side of each of the PZT disc while the PZT disc is resting on horizontal surface with the epoxy side up, or the PZT pad while the bottom case is resting on horizontal surface;
allowing the drop to self-level for a first self-leveling time period;
placing the epoxy side of each of the PZT disc on each of the PZT pad while the bottom case is resting on horizontal surface; and
allowing the PZT disc and the bottom case assembly to cure for a first cure time period.

14. The improved fetal heart rate transducer in accordance with claim 13, further comprising:
a slow-cure epoxy;
a frontend printed circuit board (PCB) having a PCB top side and a PCB epoxy side, each of the PZT disc interconnects with and are operationally related to the frontend PCB, the frontend PCB adheres to the interior surface of the bottom case as follows:
cleaning the PCB epoxy side of the frontend PCB;
mixing and degassing in a vacuum, for a second degas time period, the slow-cure epoxy;
coating the PCB epoxy side of the frontend PCB with a uniform layer of the slow-cure epoxy while the frontend PCB is resting on horizontal surface with the PCB epoxy side up;
allowing the uniform layer to self-level for a second self-leveling time period;
placing the frontend PCB in position with the PCB epoxy side in contact with the interior surface of the bottom case;
allowing the frontend PCB to self-level for a third self-leveling time period; and
clamping, for a second cure time, the frontend PCB and the bottom case at more than one of a pressure point, the pressure point are symmetrically located on surface of the top side of the frontend PCB.

15. The improved fetal heart rate transducer in accordance with claim 14, further comprising:
a backend PCB that interconnects with the frontend PCB and is fastened at perimeter of the backend PCB to the bottom case by silicone.

16. The improved fetal heart rate transducer in accordance with claim 15, the bottom case comprises one or more of a raised island pad that extends from the interior surface of the bottom case to bottom surface of the backend PCB.

17. A method of using an improved fetal heart rate transducer comprising the steps of:
coupling an index plate with an ultrasound coupling jelly to the improved fetal heart rate transducer, the index plate having more than one of a piezo-electric crystal (PZT) disc position hole corresponding to and correlated with location of each of more than one of a PZT disc within the improved fetal heart rate transducer, the improved fetal heart rate transducer comprises a top case, and a bottom case that fastens to the top case, the bottom case comprises an interior surface, the interior surface comprises more than one of a standoff, and de-embossed or raised more than one of a piezo-electric crystal (PZT) pad, more than one of a metal insert is molded into place within the standoff as the bottom case is fabricated, each of the PZT disc having a top side and an epoxy side, each of the PZT disc adheres to the PZT pad as follows:
cleaning the interior surface and the PZT disc;
mixing and degassing in a vacuum, for a first degas time period, an ultra slow-cure epoxy;
depositing a drop of the ultra slow-cure epoxy in center of the epoxy side of each of the PZT disc while the PZT disc is resting on horizontal surface with the epoxy side up, or the PZT pad while the bottom case is resting on horizontal surface;
allowing the drop to self-level for a first self-leveling time period;
placing the epoxy side of each of the PZT disc on each of the PZT pad while the bottom case is resting on horizontal surface; and
allowing the PZT disc and the bottom case assembly to cure for a first cure time period;
recording a transducer PZT disc transmit waveform for each of the PZT disc, by way of an oscilloscope that is operationally connected to a hydrophone that is in a receive mode, by placing a hydrophone PZT disc that is operationally related to the hydrophone into one of the PZT disc position hole and recording one of the transducer PZT disc transmit waveform corresponding to one of the PZT disc, and repeating by moving the hydrophone PZT disc to a different one of the PZT disc position hole until at least one of the transducer PZT disc transmit waveform has been recorded at each of the PZT disc position hole; and determining if each of the transducer PZT disc transmit waveform is similar in amplitude, frequency, and repetition rate indicating that the improved fetal heart rate transducer is transmitting properly, and indicating that each of the PZT disc is uniformly bonded to the interior surface of the bottom case of the improved fetal heart rate transducer.

18. The method in accordance with claim 17, further comprising the steps of:

recording a transducer PZT disc receive waveform for each of the PZT disc, by way of the oscilloscope that is operationally connected to output of a pre-amp of the fetal heartbeat transducer while the hydrophone is in a transmit mode, by placing the hydrophone PZT disc into one of the PZT disc position hole and recording one of the transducer PZT disc receive waveform corresponding to one of the PZT disc, and repeating by moving the hydrophone PZT disc to a different one of the PZT disc position hole until at least one of the transducer PZT disc receive waveform has been recorded for each of the PZT disc position hole; and determining if each of the transducer PZT disc receive waveform is similar in amplitude, frequency, and repetition rate indicating the improved fetal heart rate transducer is receiving properly, and that each of the PZT disc is uniformly bonded to the bottom case of the improved fetal heart rate transducer.

19. The method in accordance with claim 18, while the hydrophone is in the transmit mode of operation, only the PZT disc for which the transducer PZT disc receive waveform is being recorded is electrically connected within the improved fetal heart rate transducer and other of the PZT disc are electrically disconnected.

20. The method in accordance with claim 17, further comprising the steps of:

placing a water phantom coupled on both ends with the ultrasound coupling jelly between the index plate and the improved fetal heart rate transducer;

recording a transducer PZT disc transmit phantom waveform for each of the PZT disc, by way of the oscilloscope that is operationally connected to the hydrophone that is in the receive mode, by placing the hydrophone PZT disc that is operationally related to the hydrophone into one of the PZT disc position hole and recording one of the transducer PZT disc transmit phantom waveform corresponding to one of the PZT disc, and repeating by moving the hydrophone PZT disc to a different one of the PZT disc position hole until at least one of the transducer PZT disc transmit phantom waveform has been recorded at each of the PZT disc position hole; and determining if each of the transducer PZT disc transmit phantom waveform is similar in amplitude, frequency, and repetition rate through the water phantom indicating uniform field strength at height of the water phantom.

21. An improved fetal heart rate transducer comprising:

a top case;

a bottom case that fastens to the top case, the bottom case comprises an interior surface, the interior surface comprises de-embossed or raised more than one of a piezo-electric crystal (PZT) pad;

more than one of a PZT disc, each of the PZT disc adheres to the PZT pad;

a frontend printed circuit board (PCB) is secured to the bottom case and is operationally related to the PZT disc;

a cable having a first cable end and a second cable end;

a fetal monitor connector comprises a hollow rigid body having a wire connection end and an integrally formed grooved end;

a strain relief is placed over the first cable end and secured within the integrally formed grooved end holding the first cable end from slipping out of the hollow rigid body; and a secondary strain relief is fastened around the first cable end within the hollow rigid body proximate to the strain relief, wherein the secondary strain relief further prevents the first cable end from being pulled out of the hollow rigid body, more than one of a conductor from the first cable end terminates with electrical connections at the wire connection end;

wherein the fetal monitor connector plugs into a fetal monitor, and the second cable end terminates with a transducer connector, the transducer connector connects to the frontend PCB.

* * * * *